(12) United States Patent
Abe

(10) Patent No.: US 10,524,767 B2
(45) Date of Patent: Jan. 7, 2020

(54) ULTRASOUND DIAGNOSTIC APPARATUS AND ULTRASOUND IMAGING METHOD

(71) Applicant: Toshiba Medical Systems Corporation, Otawara-shi (JP)

(72) Inventor: Yasuhiko Abe, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 407 days.

(21) Appl. No.: 14/324,670

(22) Filed: Jul. 7, 2014

(65) Prior Publication Data

US 2015/0011882 A1 Jan. 8, 2015

(30) Foreign Application Priority Data

Jul. 8, 2013 (JP) .................................. 2013-142807

(51) Int. Cl.
| | | |
|---|---|---|
| *A61B 8/08* | (2006.01) | |
| *G01S 15/89* | (2006.01) | |
| *G01S 7/52* | (2006.01) | |

(52) U.S. Cl.
CPC .................................. *A61B 8/5207* (2013.01)

(58) Field of Classification Search
None
See application file for complete search history.

(56) References Cited

U.S. PATENT DOCUMENTS

| | | | | |
|---|---|---|---|---|
| 2003/0092989 | A1* | 5/2003 | Aichhorn | A61B 8/08 600/443 |
| 2004/0002651 | A1* | 1/2004 | Sumanaweera | G01S 15/8995 600/437 |
| 2006/0241454 | A1* | 10/2006 | Ustuner | A61B 8/4483 600/447 |
| 2012/0157850 | A1* | 6/2012 | Sumi | A61B 8/0891 600/443 |

FOREIGN PATENT DOCUMENTS

JP 2012-71115 4/2012

OTHER PUBLICATIONS

Ultrasound Imaging (Yao Wang, http://eeweb.poly.edu/~yao/EL5823/Ultrasound_imaging_ch11.pdf, Jun. 10, 2010).*
U.S. Appl. No. 14/688,373, filed Apr. 16, 2015, Abe, et al.

* cited by examiner

*Primary Examiner* — Carolyn A Pehlke
(74) *Attorney, Agent, or Firm* — Oblon, McClelland, Maier & Neustadt, L.L.P.

(57) ABSTRACT

An ultrasound diagnostic apparatus includes an acquisition unit acquiring pieces of ultrasound image data at different deflection angles; a calculation unit calculating coefficients corresponding to respective positions in ultrasound image data corresponding to a certain deflection angle based on signal or pixel values corresponding to the respective positions in at least one piece of ultrasound image data corresponding to a deflection angle other than the certain deflection angle; a multiplication unit multiplying, by the (Continued)

coefficients, signal or pixel values corresponding to the respective positions in the piece of ultrasound image data corresponding to the certain deflection angle, or signal or pixel values corresponding to the respective positions in image data obtained by compounding ultrasound image data corresponding to respective deflection angles including the certain deflection angle; and a control unit causing a display unit to display an image based on the signal or pixel values multiplied by the coefficients.

17 Claims, 15 Drawing Sheets

FIG.11A

| Lr2, Lr1, Lr0, Cr, Rr0, Rr1, Rr2 |

FIG.11B

| Lr2, Lr1, Lr0, Rr0, Rr1, Rr2 | ⇒ | MEAN SIGNAL |

FIG.11C

| Lr0, Cr, Rr0 | ⇒ | CENTRAL SIGNAL |
| Lr2, Lr1, Rr1, Rr2 | ⇒ | MEAN SIGNAL |

FIG.11D

| Lr1, Lr0, Cr, Rr0, Rr1 | ⇒ | CENTRAL SIGNAL |
| Lr2, Lr1, Rr1, Rr2 | ⇒ | MEAN SIGNAL |

FIG.13A  Lp2, Lp1, Lp0, Cp, Rp0, Rp1, Rp2

FIG.13B  Lp2, Lp1, Lp0, Rp0, Rp1, Rp2 ⇒ MEAN SIGNAL

FIG.13C  Lp0, Cp, Rp0 ⇒ CENTRAL SIGNAL
Lp2, Lp1, Rp1, Rp2 ⇒ MEAN SIGNAL

FIG.13D  Lp1, Lp0, Cp, Rp0, Rp1 ⇒ CENTRAL SIGNAL
Lp2, Lp1, Rp1, Rp2 ⇒ MEAN SIGNAL

| | FIRST SCAN MODE | SECOND SCAN MODE |
|---|---|---|
| PROCESS | M | M |
| | M | C |
| | C | M |

| | FIRST SCAN MODE | THIRD SCAN MODE |
|---|---|---|
| PROCESS | M | M |
| | M | C |
| | C | M |

FIG.19

| | SECOND SCAN MODE | THIRD SCAN MODE |
|---|---|---|
| PROCESS | M | M |
| | M | C |
| | C | M |

|  | FIRST SCAN MODE | SECOND SCAN MODE | THIRD SCAN MODE |
|---|---|---|---|
| PROCESS | M | M | M |
|  | M | M | C |
|  | M | C | M |
|  | C | M | M |
|  | M | C | C |
|  | C | M | C |
|  | C | C | M |

ULTRASOUND DIAGNOSTIC APPARATUS AND ULTRASOUND IMAGING METHOD

CROSS-REFERENCE TO RELATED APPLICATION(S)

This application is based upon and claims the benefit of priority from Japanese Patent Application No. 2013-142807, filed on Jul. 8, 2013; the entire contents of which are incorporated herein by reference.

FIELD

Embodiments described herein relate generally to an ultrasound diagnostic apparatus and an ultrasound imaging method.

BACKGROUND

Conventionally, various methods have been performed to reduce multiple-reflection echoes in an ultrasound image (B-mode image) that hinder diagnosis. As one example of such methods, a method is known of compounding, by averaging, a plurality of B-mode images at different deflection angles of ultrasound transmission and reception. A method is also known in which this method is applied for estimating the levels and the positions of multiple-reflection echo components from the B-mode images at different deflection angles to adaptively control weights for the averaging based on the estimation result.

Due to the limitation of the element factor, however, the above-described methods of compounding a plurality of images at different deflection angles are inevitably subject to the influence of amplitude reduction in elements at aperture edges, which becomes noticeable when the deflection angles are increased. Specifically, the lateral resolution of an obliquely tilted image is low due to its smaller effective aperture in comparison with an image (central image) at a regular deflection angle of "0°". Furthermore, in the obliquely tilted image, the sensitivity (S/N ratio) is also low compared with the central image. Thus, in an output image compounded with a plurality of images at different deflection angles, the lateral resolution and the sensitivity are lower than those of a regular central image.

BRIEF DESCRIPTION OF THE DRAWINGS

FIG. 10A, FIG. 10B, FIG. 10C, FIG. 10D, FIG. 10E, FIG. 11A, FIG. 11B, FIG. 11C, and FIG. 11D are diagrams illustrating the second embodiment;

FIG. 12A, FIG. 12B, FIG. 12C, FIG. 12D, FIG. 12E, FIG. 13A, FIG. 13B, FIG. 13C, and FIG. 13D are diagrams illustrating the third embodiment;

FIG. 14, FIG. 15, FIG. 16, FIG. 17, FIG. 18, FIG. 19, FIG. 20, and FIG. 21 are diagrams illustrating the fourth embodiment; and FIG. 22 is a diagram illustrating a modification.

DETAILED DESCRIPTION

An ultrasound diagnostic apparatus according to an embodiment includes an acquisition unit, a calculation unit, a multiplication unit, and a control unit. The acquisition unit acquires a plurality of pieces of ultrasound image data at different deflection angles for ultrasound transmission and reception. The calculation unit calculates coefficients corresponding to a plurality of respective positions in a piece of ultrasound image data corresponding to a certain deflection angle based on signal values or pixel values corresponding to the respective positions in at least one piece of ultrasound image data corresponding to a deflection angle other than the certain deflection angle. The multiplication unit multiplies, by the coefficients, signal values or pixel values corresponding to the respective positions in the piece of ultrasound image data corresponding to the certain deflection angle, or signal values or pixel values corresponding to the respective positions in a piece of image data that is obtained by compounding pieces of ultrasound image data corresponding to a plurality of respective deflection angles including the certain deflection angle. The control unit causes a display unit to display an image based on the signal values or the pixel values multiplied by the coefficients.

An ultrasound diagnostic apparatus according to embodiments will be explained in detail below with reference to accompanying drawings.

First Embodiment

Figure 1:
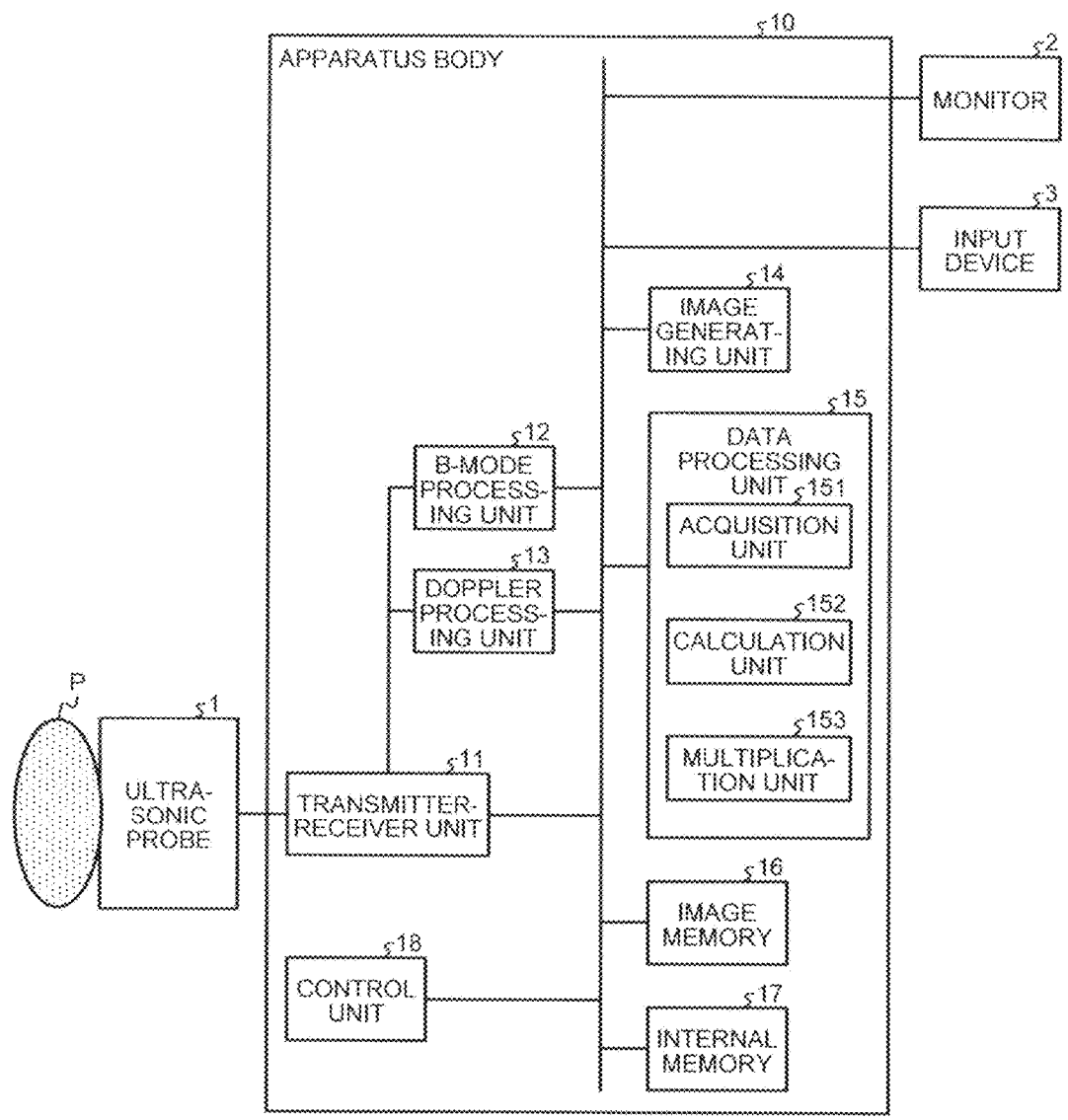
FIG. 1 is a block diagram illustrating a configuration example of an ultrasound diagnostic apparatus according to a first embodiment.

The configuration of an ultrasound diagnostic apparatus according to a first embodiment will be first described. FIG. 1 is a block diagram illustrating a configuration example of the ultrasound diagnostic apparatus according to the first embodiment. As illustrated in FIG. 1, the ultrasound diagnostic apparatus according to the first embodiment includes an ultrasonic probe 1, a monitor 2, an input device 3, and an apparatus body 10.

The ultrasonic probe 1 includes a plurality of transducer elements (e.g., piezoelectric transducer elements). The transducer elements generate ultrasonic waves based on a drive signal supplied from a transmitter-receiver unit 11 included in the apparatus body 10 described later. The transducer elements included in the ultrasonic probe 1 receive a reflected wave from a subject P to convert the reflected wave thus received into an electric signal. The ultrasonic probe 1 also includes matching layers provided to the transducer elements and backing materials preventing ultrasonic waves from traveling behind the transducer elements, for example.

When ultrasonic waves are transmitted from the ultrasonic probe 1 to the subject P, the ultrasonic waves thus transmitted are sequentially reflected on the planes of discontinuity of acoustic impedances in body tissues of the subject P and then received by the transducer elements included in the ultrasonic probe 1 as reflected wave signals. The amplitudes of the reflected wave signals thus received depend on the differences between the acoustic impedances on a plane of discontinuity on which the ultrasonic waves are reflected. When the ultrasonic pulses transmitted are reflected on a moving blood flow or the surface of a cardiac wall, for example, the reflected wave signals undergoes a frequency shift depending on the velocity component in the ultrasound transmission direction of the moving body because of the Doppler effect.

The ultrasonic probe 1 is removably connected to the apparatus body 10. To two-dimensionally scan the subject P, an operator connects, for example, a one-dimensional array probe in which a plurality of piezoelectric transducer elements are arranged in a line, as the ultrasonic probe 1, to the apparatus body 10. Examples of the one-dimensional array probe include a linear ultrasonic probe, a convex ultrasonic probe, and a sector ultrasonic probe. To three-dimensionally scan the subject P, an operator connects, for example, a mechanical four-dimensional probe or a two-dimensional array probe as the ultrasonic probe 1 to the apparatus body 10. A mechanical four-dimensional probe can perform two-dimensional scanning using a plurality of piezoelectric transducer elements that are arranged in a line similarly to the one-dimensional array probe, and can also perform three-dimensional scanning by causing the piezoelectric transducer elements to oscillate with a certain angle (oscillation angle). A two-dimensional array probe can perform three-dimensional scanning with a plurality of piezoelectric transducer elements that are arranged in a matrix, and can also perform two-dimensional scanning by converging and transmitting ultrasound waves. The following describes a case in which the apparatus body 10 is connected to a one-dimensional array probe.

The input device 3 includes a mouse, a keyboard, buttons, a panel switch, a touch command screen, a foot switch, a track ball, or a joystick. The input device 3 receives various setting requests from the operator of the ultrasound diagnostic apparatus and transmits the received setting requests to the apparatus body 10.

The monitor 2 displays a graphical user interface (GUI) through which the operator of the ultrasound diagnostic apparatus inputs various setting requests using the input device 3 and displays ultrasonic image data generated by the apparatus body 10, for example.

The apparatus body 10 is an apparatus that generates ultrasonic image data based on the reflected wave signal received by the ultrasonic probe 1. The apparatus body 10 illustrated in FIG. 1 is an apparatus that can generate two-dimensional ultrasound image data based on two-dimensional reflected wave data received by the ultrasonic probe 1. The apparatus body 10 illustrated in FIG. 1 is also an apparatus that can generate three-dimensional ultrasound image data based on three-dimensional reflected wave data received by the ultrasonic probe 1.

As illustrated in FIG. 1, the apparatus body 10 includes the transmitter-receiver unit 11, a B-mode processing unit 12, a Doppler processing unit 13, an image generating unit 14, a data processing unit 15, an image memory 16, an internal memory 17, and a control unit 18.

The transmitter-receiver unit 11 is a transmission beam former that controls transmission directionality in transmitting ultrasound waves. Specifically, the transmitter-receiver unit 11 includes a rate pulse generator, a transmission delay unit, and a transmission pulser and supplies a drive signal to the ultrasonic probe 1. The rate pulse generator repeatedly generates rate pulses for forming an ultrasonic wave for transmission at a predefined rate frequency (pulse repetition frequency, PRF). The rate pulses pass through the transmission delay unit, thereby applying voltage to the transmission pulser in a manner having different transmission delay times. The transmission delay unit provides each rate pulse generated by the rate pulse generator with a transmission delay time for each transducer element. The transmission delay time is required to converge ultrasonic waves generated by the ultrasonic probe 1 into a beam to determine transmission directionality. The transmission pulser applies a drive signal (drive pulse) to the ultrasonic probe 1 at the timing based on this rate pulse.

The drive pulse is transmitted from the transmission pulser to the transducer element in the ultrasonic probe 1 via a cable, and is then converted from an electric signal into a mechanical vibration in the transducer element. This mechanical vibration is transmitted as an ultrasound wave inside an organism. Ultrasound waves having different transmission delay times for the respective transducer elements are converged and transmitted in a certain transmission direction. The transmission delay unit adjusts the transmission direction from the surface of the transducer elements as required by changing the transmission delay time provided to each rate pulse. The transmitter-receiver unit 11 provides transmission directionality by controlling the number and positions (transmission aperture) of transducer elements used for transmission of an ultrasound beam and transmission delay times corresponding to the positions of the respective transducer elements constituting the transmission aperture.

The transmitter-receiver unit 11 has functions capable of instantaneously changing transmission frequencies, transmission drive voltages, and the like in order to perform a predefined scan sequence based on an instruction from the control unit 18 described below. In particular, the transmission drive voltages can be changed with a linear amplifier type of transmission circuit capable of instantaneously changing values or a mechanism for electrically switching over a plurality of power source units.

The reflected waves of the ultrasound waves transmitted by the ultrasonic probe 1 are converted from mechanical vibrations to electric signals (reflected wave signals) at the transducer elements after reaching the transducer elements in the ultrasonic probe 1. The reflected wave signals are input via the cable to the transmitter-receiver unit 11 serving as a reception beam former that controls reception directionality in receiving ultrasound waves.

More specifically, the transmitter-receiver unit 11 includes an amplifier circuit, an analog/digital (A/D) converter, a reception delay circuit, and an adder, and performs various processing on the reflected wave signals received by the ultrasonic probe 1 to generate reflected wave data. The amplifier circuit amplifies the reflected wave signals for each channel and perform thereon gain correction processing. The A/D converter A/D-converts the reflected wave signals thus gain-corrected. The reception delay circuit provides digital data with a reception delay time required to determine reception directionality. The adder performs addition processing on the reflected wave signals provided with the reception delay time by the reception delay circuit to generate reflected wave data. The addition processing performed by the adder enhances reflection components from the direction in accordance with the reception directionality of the reflected wave signals. The transmitter-receiver unit 11 provides reception directionality by controlling the number and positions (reception aperture) of transducer elements used for reception of reflected waves and reception delay times corresponding to the positions of the respective transducer elements constituting the reception aperture.

The transmitter-receiver unit 11 causes the ultrasonic probe 1 to transmit two-dimensional ultrasonic beams when the subject P is two-dimensionally scanned. The transmitter-receiver unit 11 then generates two-dimensional reflected wave data from two-dimensional reflected wave signals received by the ultrasonic probe 1. The transmitter-receiver unit 11 also causes the ultrasonic probe 1 to transmit three-dimensional ultrasonic beams when the subject P is three-dimensionally scanned. The transmitter-receiver unit 11 then generates three-dimensional reflected wave data from three-dimensional reflected wave signals received by the ultrasonic probe 1.

The form of each output signal from the transmitter-receiver unit 11 can be selected from various forms such as a signal including phase information and a signal indicating amplitude information after envelope demodulation. The signal including phase information herein is an IQ signal that includes an in-phase signal (I signal) and a quadrature-phase signal (Q signal), or a radio frequency (RF) signal.

The B-mode processing unit 12 performs logarithmic amplification, envelope demodulation, and logarithmic compression, for example, on the reflected wave data output by the transmitter-receiver unit 11 to generate data (B-mode data) in which the signal intensity (amplitude intensity) for each sample point is represented by the brightness of its luminance.

The Doppler processing unit 13 performs frequency analysis on the reflected wave data output by the transmitter-receiver unit 11 to generate data (Doppler data) that includes extracted pieces of kinetic information of moving bodies (blood flows, tissues, contrast agent echo components, etc.) based on the Doppler effect. Specifically, the Doppler processing unit 13 generates Doppler data including average velocities, variances, and power values, for example, extracted at multiple points as the pieces of kinetic information of moving bodies.

The B-mode processing unit 12 and the Doppler processing unit 13 can process both two-dimensional reflected wave data and three-dimensional reflected wave data.

The image generating unit 14 generates ultrasound image data from the data generated by the B-mode processing unit 12 and the Doppler processing unit 13. Specifically, the image generating unit 14 generates two-dimensional B-mode image data in which the intensity of a reflected wave is represented by the luminance from the two-dimensional B-mode data generated by the B-mode processing unit 12. The image generating unit 14 also generates two-dimensional Doppler image data representing moving body information from the two-dimensional Doppler data generated by the Doppler processing unit 13. The two-dimensional Doppler image data includes velocity image data, dispersion image data, power image data, or image data in which the data mentioned above are combined.

The image generating unit 14 typically generates ultrasonic image data for display through conversion (scan-conversion) of signal arrays of ultrasonic scan lines into signal arrays of scan lines in a video format represented by television, for example. Specifically, the image generating unit 14 generates ultrasonic image data for display through coordinate conversion in accordance with the form of the ultrasonic scan performed by the ultrasonic probe 1. The image generating unit 14 also performs various image processing other than the scan conversion. For example, the image generating unit 14 uses a plurality of image frames after the scan conversion to perform image processing reproducing an image having an average luminance (smoothing processing) and image processing using a differentiation filter in an image (edge enhancement processing). The image generating unit 14 also combines text information on various parameters, scales, body marks, and the like with ultrasonic image data.

In other words, the B-mode data and the Doppler data are ultrasonic image data before the scan conversion, and data generated by the image generating unit 14 is ultrasonic image data for display after the scan conversion. The B-mode data and the Doppler data are also referred to as raw data.

The image generating unit 14 further generates three-dimensional B-mode image data by performing coordinate conversion on the three-dimensional B-mode data generated by the B-mode processing unit 12. The image generating unit 14 also generates three-dimensional Doppler image data by performing coordinate conversion on the three-dimensional Doppler data generated by the Doppler processing unit 13. In other words, the image generating unit 14 generates "three-dimensional B-mode image data and three-dimensional Doppler image data" as "three-dimensional ultrasonic image data (volume data)". The image generating unit 14 further performs various types of rendering processing on volume data to generate various two-dimensional image data for causing the monitor 2 to display volume data.

The data processing unit 15 is a processing unit that performs various processes on the data generated in the apparatus body 10, and includes an acquisition unit 151, a calculation unit 152, and a multiplication unit 153 as illustrated in FIG. 1. The data processing unit 15 according to the first embodiment uses the ultrasound image data generated by the image generating unit 14 as data to be processed. The data processing unit 15 according to the first embodiment will be described later in detail.

The image memory 16 is a memory storing therein image data generated by the image generating unit 14. The image memory 16 also can store therein data generated by the B-mode processing unit 12 and the Doppler processing unit 13. The B-mode data and the Doppler data stored in the image memory 16 can be called by the operator after diagnosis, for example, and serve as ultrasonic image data for display after going through the image generating unit 14. The image memory 16 also can store therein the data output from the transmitter-receiver unit 11 and the data output from the data processing unit 15.

The internal memory 17 stores therein various data such as control programs for performing transmission and reception of ultrasonic waves, image processing, and display processing; diagnostic information (subjects' IDs and doctors' opinions, for example); a diagnostic protocol; and various body marks. The internal memory 17 is also used for storing the data stored in the image memory 16, for example, as necessary.

The control unit 18 controls the entire processing performed by the ultrasound diagnostic apparatus. Specifically, the control unit 18 controls processing performed by the transmitter-receiver unit 11, the B-mode processing unit 12, the Doppler processing unit 13, the image generating unit 14, and the data processing unit 15 based on various setting requests input by the operator through the input device 3 and various control programs and data read from the internal memory 17. The control unit 18 also controls the monitor 2 to display ultrasonic image data for display stored in the image memory 16.

In the foregoing, the overall structure of the ultrasound diagnostic apparatus according to the first embodiment has been described. In this structure, generation and display of ultrasound image data (e.g., B-mode image data) are performed.

Figure 2:
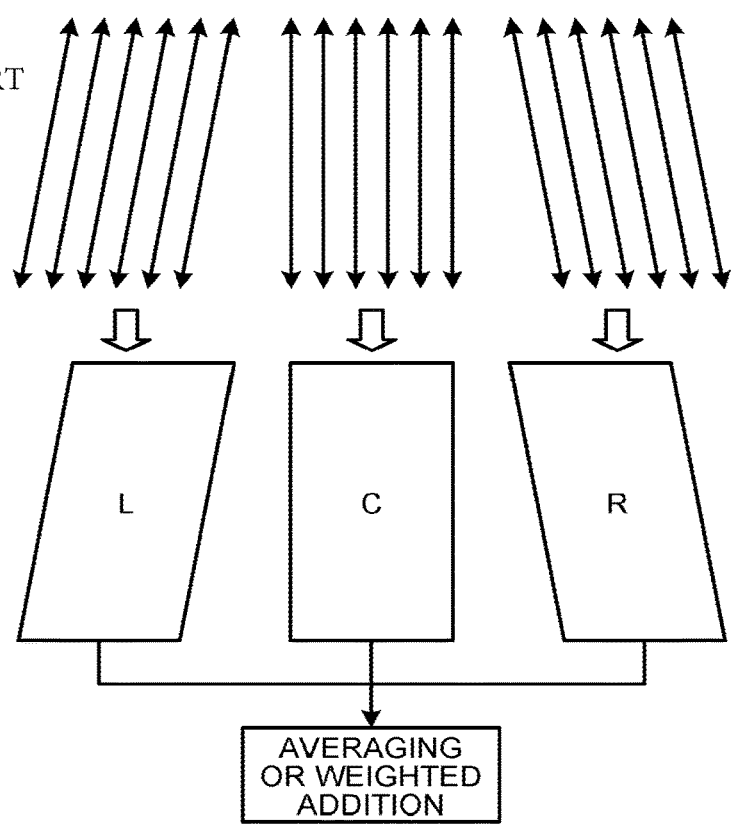
FIG. 2, FIG. 3A, and FIG. 3B are diagrams illustrating another conventional method.
Figure 3A:
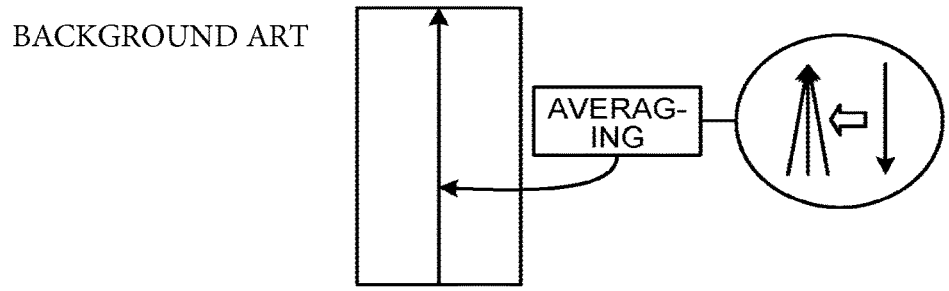
Figure 3B:
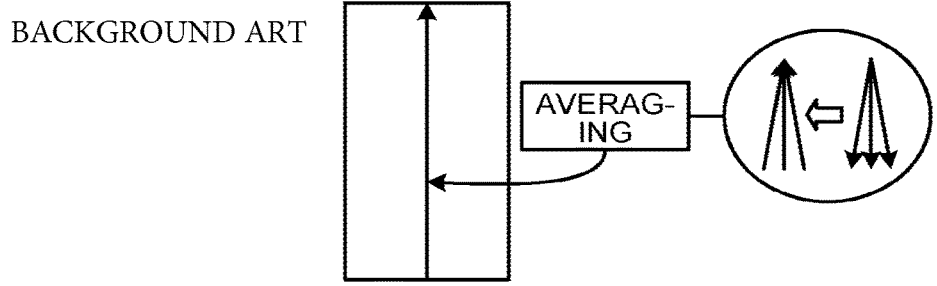

Conventionally, various methods have been performed to reduce multiple-reflection echoes that hinder diagnosis in B-mode images. These conventional methods are methods to reduce multiple-reflection echoes by what is called a spatial compounding process. FIG. 2, FIG. 3A, and FIG. 3B are diagrams illustrating such conventional methods.

One example of these methods is a method of compounding, by averaging, a plurality of pieces of B-mode image data at different deflection angles for ultrasound transmission and reception. A method is also known in which this method is applied for estimating the levels and the positions of multiple-reflection echo components from the pieces of B-mode image data at different deflection angles to adaptively control weight for the averaging based on the estimation result. These methods are methods of compounding a plurality of pieces of ultrasound image data at different deflection angles that are generated by ultrasound scanning for making deflection angles for ultrasound transmission and reception different between frames.

The deflection angle of a direction that is perpendicular to the array direction of the transducer elements is defined as "0°". The deflection angle "0°" indicates a direction of regular ultrasound transmission and reception that are performed without deflection applied. A deflection angle of a direction that is tilted to the left relative to the array direction of the transducer elements is defined as a "positive angle", and a deflection angle of a direction that is tilted to the right relative to the array direction of transducer elements is defined as a "negative angle".

With these definitions, "C" indicated in FIG. 2 denotes a piece of B-mode image data generated by performing ultrasound transmission and reception at the deflection angle "0°". "L" indicated in FIG. 2 denotes a piece of B-mode image data generated by performing ultrasound transmission and reception that are deflected left at a deflection angle of "+θ°". "R" indicated in FIG. 2 denotes a piece of B-mode image data generated by performing ultrasound transmission and reception that are deflected right at a deflection angle of "−θ°". Hereinafter, the "L" indicated in FIG. 2 is referred to as left-deflection image data L. The "R" indicated in FIG. 2 is referred to as right-deflection image data R. "C" indicated in FIG. 2 that denotes an image in the middle between the left-deflection image data L and the right-deflection image data R is referred to as central image data C.

In the conventional method illustrated in FIG. 2, image data is output that is obtained by averaging the central image data C, the left-deflection image data L, and the right-deflection image data R. Alternatively, in the conventional method illustrated in FIG. 2, the levels and the positions of multiple-reflection echo components are estimated from the central image data C, the left-deflection image data L, and the right-deflection image data R. Subsequently, in the conventional method illustrated in FIG. 2, weights for the averaging are calculated based on the estimated result, and weighted addition is performed of the central image data C, the left-deflection image data L, and the right-deflection image data R to output the resulting image data.

Other than the above-described conventional methods of compounding a plurality of images at different deflection angles, two conventional methods illustrated in FIGS. 3A and 3B are used as general spatial compounding for reducing multiple-reflection echoes. The method illustrated in FIG. 3A is a method of averaging a group of a plurality of received signals at different reception deflection angles that are simultaneously obtained by parallel simultaneous reception in response to the same transmission beam when received signals on one scan line are obtained. In the method illustrated in FIG. 3A, simultaneously received signals in three directions are obtained by parallelly and simultaneously receiving reflected waves at reception deflection angles (e.g., 0°, +θ°, −θ°) in the three directions in response to an ultrasound wave transmitted on a certain scan line with the transmission aperture and the reception aperture being fixed. In the conventional method illustrated in FIG. 3A, one received signal at a reception deflection angle of "0°" is obtained by averaging the simultaneously received signals in three directions. This processing is performed for all scan lines in a frame.

In contrast, the method illustrated in FIG. 3B is a method in which, when a received signal on one scan line is obtained, received signals from corresponding directions are obtained at transmission deflection angles that are different between rates, and the resulting received signals at these rates are averaged. In FIG. 3B, received signals in three directions are depicted that are generated by performing ultrasound transmission and reception at deflection angles (0°, +θ°, −θ°) in three directions with the transmission aperture and the reception aperture being fixed. In the conventional method illustrated in FIG. 3B, one received signal at a reception deflection angle of "0°" is obtained by averaging the received signals in three directions. This processing is performed for all scan lines in a frame.

These three types of conventional methods are techniques for improving a signal-to-noise ratio in an image by utilizing a fact that, when a deflection angle of an ultrasound beam relative to the subject P is changed (when the ultrasound beam is tilted), the position where multiple-reflection echoes (noise) appear changes depending on the deflection angle, and by performing a compounding process to maintain signal components (e.g., tissue-derived signal components) intensity of which changes relatively little even when the ultrasound beam is tilted.

The conventional method illustrated in FIG. 3A is excellent in real-time performance because parallel simultaneous reception is used. However, the conventional method illustrated in FIG. 3A requires larger deflection angles to obtain a multiple reduction effect because deflection angles are made different between transmission and reception. However, in the conventional method illustrated in FIG. 3A, the sensitivity decreases when the deflection angles between transmission and reception are increased.

In contrast, in the conventional method illustrated in FIG. 3B, because deflection angles between transmission and reception can be set the same, larger deflection angles are set while the sensitivity reduction is being prevented, and thus a multiple reduction effect can be obtained that is greater than the conventional method illustrated in FIG. 3A. However, the conventional method illustrated in FIG. 3B requires a rate sequence, thereby reducing the frame rate.

In contrast, in the conventional method illustrated in FIG. 2, because the deflection angle is changed on a frame-by-frame basis, deflection angles can be set the same between transmission and reception, and thus the frame rate is not reduced while the sensitivity reduction is being prevented. Thus, in the conventional method illustrated in FIG. 2, the multiple reduction effect, the frame rate, and a certain level of sensitivity can be maintained.

Due to the limitation of the element factor, however, such a method in which the deflection angle is changed on a frame-by-frame basis is inevitably subject to the influence of amplitude reduction in elements at aperture edges, which becomes noticeable when the deflection angle is increased. In particular, in elements at the edges of the apertures, transmission and reception are performed with relatively larger deflection angles, whereby the amplitude reduction is larger. This corresponds to reduction in effective width of the apertures. Specifically, the lateral resolution of obliquely tilted image data (e.g., the left-deflection image data L or the right-deflection image data R) is lower than that of an image (the central image data C) at a deflection angle of "0°". Furthermore, in the obliquely tilted image, the sensitivity (S/N ratio) is also lower than that of the central image data C. Thus, in an output image compounded from a plurality of images at different deflection angles, there is a problem in that the lateral resolution and the sensitivity are lower than those of a non-deflected image (e.g., the central image data C).

Accordingly, in the ultrasound diagnostic apparatus according to the first embodiment, to obtain a high-quality image in which multiple reflections are reduced and the lateral resolution and the sensitivity are maintained, the data processing unit 15 and the control unit 18 perform processes described below.

The acquisition unit 151 according to the first embodiment acquires a plurality of pieces of ultrasound image data at different deflection angles for ultrasound transmission and reception. The acquisition unit 151 acquires a plurality of pieces of ultrasound image data that are generated by ultrasound scanning in which a deflection angle for ultrasound transmission and reception is changed between frames. For example, the acquisition unit 151 acquires an image data group including the pieces of ultrasound image data at different deflection angles that are generated by the ultrasound scanning in which a deflection angle of ultrasound transmission and reception is changed between frames. The calculation unit 152 according to the first embodiment then calculates coefficients corresponding to a plurality of respective positions in a piece of ultrasound image data corresponding to a certain deflection angle, based on signal values or pixel values corresponding to the respective positions in at least one piece of ultrasound image data corresponding to a deflection angle other than the certain deflection angle. The coefficients corresponding to the respective positions are represented by a coefficient distribution. For example, the calculation unit 152 calculates the coefficient distribution using at least one piece of ultrasound image data at a deflection angle in a direction other than a certain direction in the image data group. For example, the calculation unit 152 calculates the above-described coefficients (the above-described coefficient distribution) based on a mean value between pieces of data to be processed. For example, the calculation unit 152 calculates the above-described coefficients (the above-described coefficient distribution) using a function including arithmetic processing of exponentiating an input value. The multiplication unit 153 according to the first embodiment then multiplies, by the coefficients, signal values or pixel values corresponding to the respective positions in the piece of ultrasound image data corresponding to the certain deflection angle, or signal values or pixel values corresponding to the respective positions in a piece of image data that is obtained by compounding pieces of ultrasound image data corresponding to a plurality of respective deflection angles including the certain deflection angle. For example, the multiplication unit 153 multiplies, by the coefficient distribution, a piece of ultrasound image data at a deflection angle in the certain direction, or a piece of image data that is obtained by compounding pieces of ultrasound image data at respective deflection angles in a plurality of directions including the certain direction. For example, the multiplication unit 153 performs multiplication processing on data obtained by weighted addition as the above-described compounding process. The control unit 18 according to the first embodiment then causes the monitor 2 to display an image based on the signal values or the pixel values multiplied by the coefficients. For example, the control unit 18 causes the monitor 2 to display the output data from the multiplication unit 153 as ultrasound image data.

The following describes concrete examples of processes performed by the data processing unit 15 and the control unit 18 according to the first embodiment with reference to FIGS. 4A to 9D, for example. FIGS. 4A to 9D are diagrams illustrating the first embodiment.

Figure 4A:
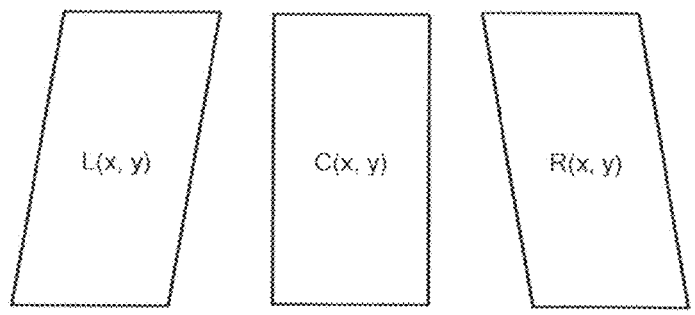
FIG. 4A, FIG. 4B, FIG. 4C, FIG. 4D, FIG. 5, FIG. 6, FIG. 7, FIG. 8, FIG. 9A, FIG. 9B, FIG. 9C, and FIG. 9D are diagrams illustrating the first embodiment.

For example, under the control of the control unit 18, the transmitter-receiver unit 11 causes the ultrasonic probe 1 to perform ultrasound transmission and reception in three directions (deflection angles: 0°, +δ°, −θ°) on a frame-by-frame basis. This causes the image generating unit 14 to generate three pieces of B-mode image data at different deflection angles. The above-described certain direction herein is the direction at the deflection angle "0°". The acquisition unit 151 then acquires these three pieces of B-mode image data. "L(x,y)" and "R(x,y)" indicated in FIG. 4A are respectively left-deflection image data and right-deflection image data in which multiple reflection components are reduced by oblique transmission and reception. "C(x,y)" indicated in FIG. 4A is B-mode image data in the direction of the deflection angle "0°", and is front image data (central image data) in which the lateral resolution and the sensitivity are high but multiple reflections may have occurred. "(x,y)" herein indicates the position of each pixel constituting the image data.

Figure 4B:
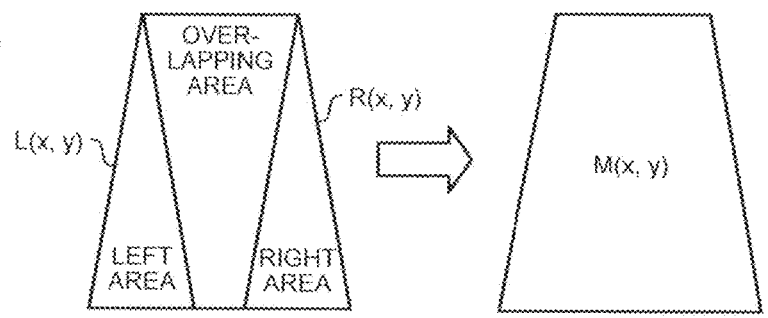

The following describes a case in which the calculation unit 152 calculates the coefficient distribution using "L(x,y)" and "R(x,y)" as objects to be processed and the multiplication unit 153 uses "C(x,y)" as an object to be multiplied. To begin with, the calculation unit 152 obtains "M(x,y)" that is mean image data of "L(x,y)" and "R(x,y)" as illustrated in FIG. 4B. Specifically, the calculation unit 152 obtains "M(x,y)" according to Formula (1):

$$M(x, y) = (L(x, y) + R(x, y))/2 \quad \text{(overlapping area)} \\ = L(x, y) \quad \text{(left area)} \\ = R(x, y) \quad \text{(right area)} \quad (1)$$

As illustrated in 4B, when "L(x,y)" and "R(x,y)" are aligned, there are an overlapping area where they overlap each other, a left area that is an area in "L(x,y)" excluding the overlapping area, a right area that is an area in "R(x,y)" excluding the overlapping area. Formula (1) above indicates that the mean image data "M(x,y)" is obtained by assigning the mean values of pixel values of "L(x,y)" and "R(x,y) at the same position for the overlapping area, assigning pixel values of "L(x,y)" for the left area, and assigning pixel values of "R(x,y)" for the right area.

Figure 4C:
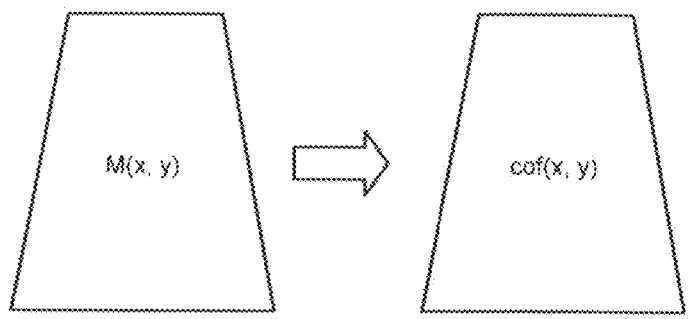

The calculation unit 152 then calculates a coefficient distribution "cof(x,y)" from the mean image data "M(x,y)" as illustrated in FIG. 4C. Specifically, the calculation unit 152 calculates "cof(x,y)" according to Formula (2):

$$cof(x, y) = (M(x, y)/\beta)^\alpha \\ (\text{when } M(x, y) > \beta, cof(x, y) = 1.0) \quad (2)$$

In Formula (2) above, the value obtained by raising a quotient of M(x,y) divided by "β" to the "power of α" is defined as "cof(x,y)". In Formula (2) above, "cof(x,y)" is defined to be "1" when the quotient of M(x,y) divided by "β" is larger than "1". "α" and "β" herein are values that are set in advance. Specifically, "β" means an upper limit of output signals, and is set equal to or smaller than the maximum value "max" of image signals. "β" is preferably set to about 70% to 80% of "max". "α" is preferably set to a value of about "¼ to ⅓".

Figure 5:
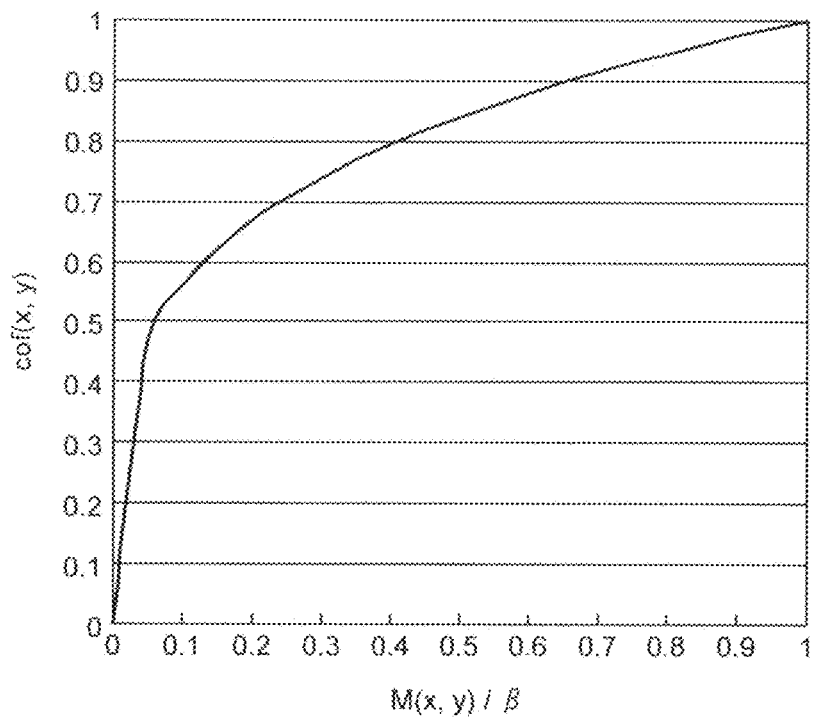

The graph illustrated in FIG. 5 is a graph in which output values "cof(x,y)" are plotted that are calculated from input values "M(x,y)/β" by using Formula (2) with "α=¼". Advantages will be described later of calculating the coefficient distribution using a function including arithmetic processing of exponentiating an input value such as Formula (2).

Figure 4D:
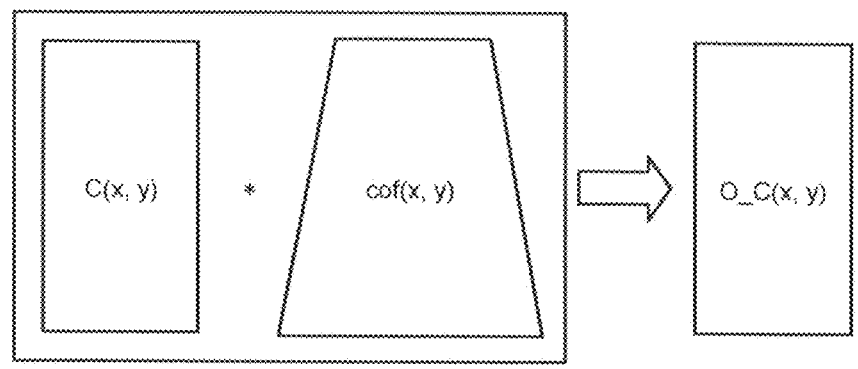

The multiplication unit 153 then multiplies the central image data "C(x,y)" by the coefficient distribution "cof(x,y)" to output the output image data "O_C(x,y)" as illustrated in FIG. 4D. Specifically, the multiplication unit 153 performs arithmetic processing of Formula (3):

$$O\_C(x,y)=C(x,y)*cof(x,y) \tag{3}$$

Figure 6:
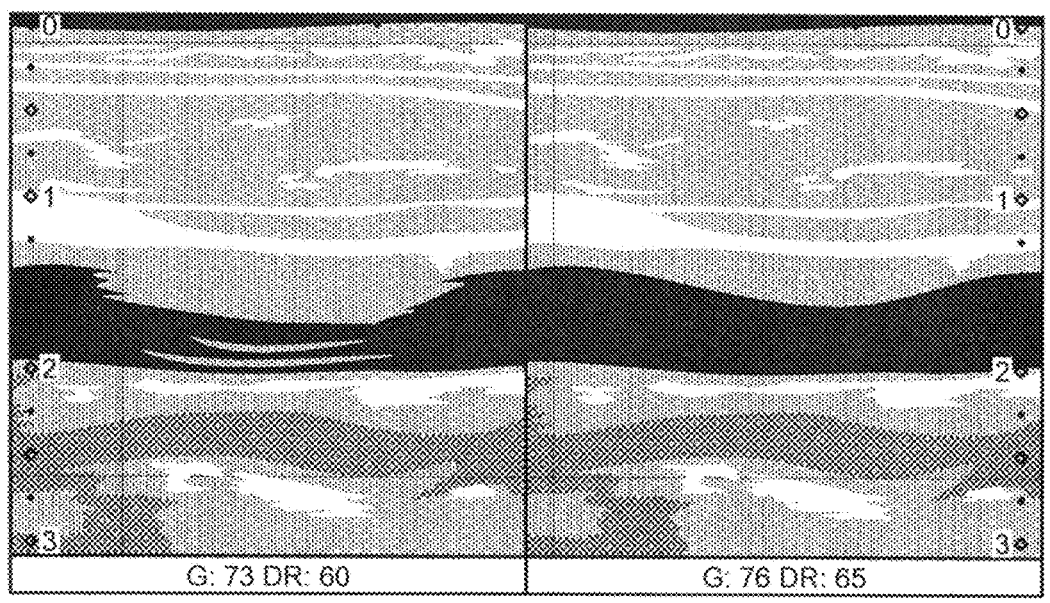

The control unit 18 then causes the monitor 2 to display the output image data "O_C(x,y)" as B-mode image data on which correction processing is performed. The left diagram in FIG. 6 illustrates front B-mode image data "C(x,y)" at the "deflection angle: 0°" out of pieces of B-mode image data in three directions that are obtained by using a linear probe to image an area including carotid arteries. The right diagram in FIG. 6 illustrates output image data "O_(x,y)" obtained by the above-described processing. As illustrated in FIG. 6, multiple reflection components appearing in carotid arteries in "C(x,y)" are reduced in "O_C(x,y)" while the lateral resolution and the sensitivity are being maintained. FIG. 6 herein illustrates a result of processing performed with settings of "α=¼, β=192, max=255, θ=10°".

The following describes reasons why "O_C(x,y)" output by the above-described processing becomes high-quality image data in which multiple reflections are reduced and also the lateral resolution and the sensitivity are maintained.

As with scattered signals, in a region where a signal level does not differ regardless of whether the region is viewed from the right or the left, the luminance of mean image data becomes high. In contrast, as with multiple reflections, in a region where a signal level is reduced by tilting a beam, the luminance of the mean image data decreases. In particular, multiple reflections cause not only reductions in signal level due to deflection to the right and the left, but also changes in the appearance position corresponding to deflection to the right and the left. Accordingly, the degree of luminance reduction in the mean image data of the left-deflection image data and the right-deflection image data increases.

Thus, in the above-described processing, in a region where the average luminance in the mean image data is high, which is considered to be an actual signal component, the coefficient value contributing to the central image data to be finally output is made larger. In the above-described processing, in a region where the average luminance in the mean image data is low, which is considered to be a noise component due to multiple reflections or the like, the coefficient value contributing to the central image data is made smaller. Thus, the above-described processing enables reduction of multiple reflection components that is effective for the central image data. The image signal itself of the output image data derives from the central image data in which the lateral resolution is high and the sensitivity is also high, and thus the lateral resolution and the sensitivity are maintained in a region for which the coefficient value is large because of being considered to be a signal.

In a conversion method for obtaining coefficient values as output data from the mean image data as input data, it is desired that, while an output value in a signal area is maintained at a high level compared with a level used as a boundary level between a signal and a noise based on magnitudes of input, an output value in a noise area be sufficiently smaller than the boundary level. A simplest method to obtain such conversion characteristics is threshold processing in which the output value is set to be "1" when the input value exceeds a preset threshold and the output value is set to be "0" when the input value is equal to or smaller than the threshold.

However, such a "boundary level between a signal and a noise" used for threshold setting generally varies depending on a subject P, and thus cannot be clearly determined. In view of this, to obtain a robust multiple reduction effect, it is effective to use conversion characteristics that smoothly change in response to an input and include characteristics that are similar to those of the threshold processing.

A specific method for obtaining such conversion characteristics preferably provides an output value according to a "power function" depending on the input level as indicated in Formula (2) above. For example, in the conversion characteristic illustrated in FIG. 5, the coefficient value smoothly changes in a range where "M(x,y)/β" is larger than "0.1", and the coefficient value significantly decreases in a range where "M(x,y)β" is equal to or smaller than "0.1".

However, when the above-described coefficient control is performed, as is clear from the graph in FIG. 5, the output image data "O_C(x,y)" indicates almost no signal in a low-luminance area, and thus there is apparently a tendency that the display dynamic range is narrowed and the gain decreases. Accordingly, the control unit 18 according to the first embodiment may control the display dynamic range and the gain when displaying the output image data using a predetermined look-up table (LUT) so that the apparent display dynamic range and the apparent gain may become equivalent to those of image data on which the above-described multiplication processing is not performed.

For example, as illustrated in FIG. 6, the control unit 18 expands the "display dynamic range: DR" of the output image data to "65 dB" when the "display dynamic range: DR" of the central image data is "60 dB". Furthermore, for example, as illustrated in FIG. 6, the control unit 18 raises the "gain: G" of the output image data to "76 dB" when the "gain: G" of the central image data is "73 dB".

Figure 7:
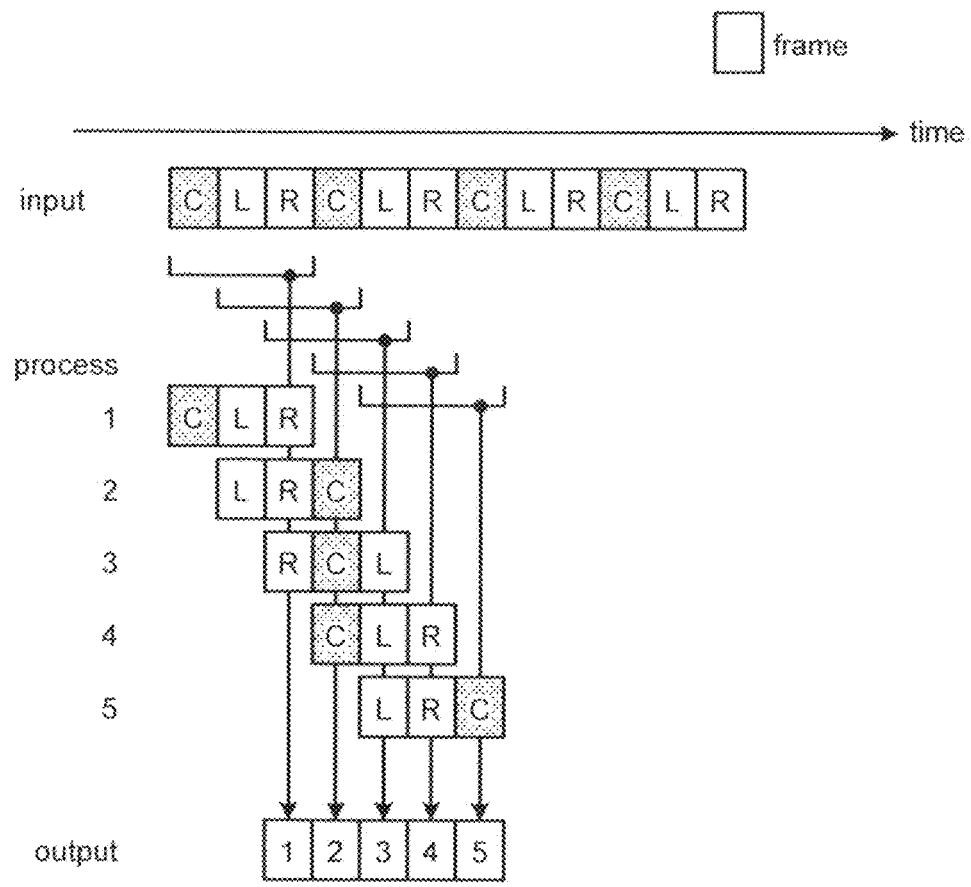

The control unit 18 controls the frame rate of the output image data (hereinafter, O_C) so that it may become approximately the same as the frame rate in regular B-mode imaging. FIG. 7 illustrates a case in which the central image data (hereinafter, C), the left-deflection image data (hereinafter, L), and the right-deflection image data (hereinafter, R) are repeatedly generated in the order of "C, L, and R" (see the row of "input" in FIG. 7). In FIG. 7, each frame is depicted by one rectangle.

In this case, the control unit 18 causes the data processing unit 15 to output "O_C" of the first frame using an image data group "C,L,R" that is initially obtained (see "process: 1" and "output: 1" in FIG. 7). The control unit 18 also causes the data processing unit 15 to output "O_C" of the second frame using an image data group "L,R,C" that includes newly generated "C" as latest data (see "process: 2" and "output: 2" in FIG. 7). The control unit 18 also causes the data processing unit 15 to output "O_C" of the third frame using an image data group "R,C,L" that includes newly generated "L" as latest data (see "process: 3" and "output: 3" in FIG. 7). The control unit 18 also causes the data processing unit 15 to output "O_C" of the fourth frame using an image data group "C,L,R" that includes newly generated "R" as latest data (see "process: 4" and "output: 4" in FIG. 7). The control unit 18 also causes the data processing unit 15 to output "O_C" of the fifth frame using an image data group "L,R,C" that includes newly generated "C" as latest data (see "process: 5" and "output: 5" in FIG. 7). Performing such control can maintain the frame rate.

Figure 8:
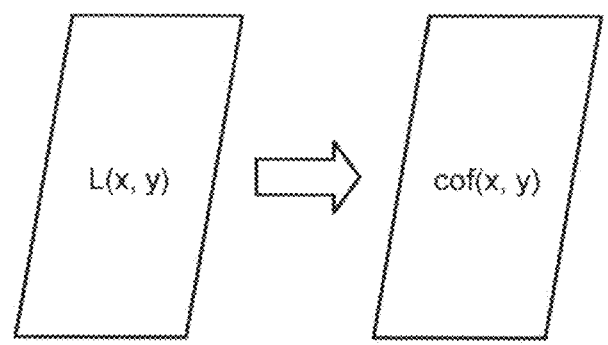

In the foregoing, a typical example has been described in which deflection angles in three directions (±θ° and 0°) are used, and the mean image data of the left-deflection image data and the right-deflection image data is used to calculate a coefficient distribution. However, "oblique-deflection image data" for calculating the coefficient distribution for performing multiple reduction may be deflection image data in one direction, either to the right or to the left. For example, the calculation unit 152 may substitute "L(x,y)" for Formula (2) to calculate the coefficient distribution "cof(x,y)" as illustrated in FIG. 8.

Because a structure that can be a multiple reflection source in a scanning area of the subject P may be tilted obliquely to the array direction of the transducer elements, it is preferable that the mean image data of the left-deflection image data and the right-deflection image data be used as described above to obtain a robust multiple-reflection reduction effect. As described with reference to FIG. 4B, the left-deflection image data is used as the mean image data for the left area excluding the overlapping area, and the right-deflection image data is used as the mean image data for the right area excluding the overlapping area. Even in such a case, however, as described with reference to the drawings including FIG. 6, output image data can be obtained in which multiple reflections are reduced and also the lateral resolution and the sensitivity are maintained.

Furthermore, the first embodiment allows the number of directions of deflection angles to be increased to five or seven. In this case, it is possible to perform "(a): a method of increasing the number of directions for addition of mean image data", "(b): a method of using, as central image data, image data that is obtained by performing a compounding process (e.g., weighting process) on a plurality of pieces of image data including front image data", and "(c): a method achieved by combining (a) and (b)".

Figure 9A:
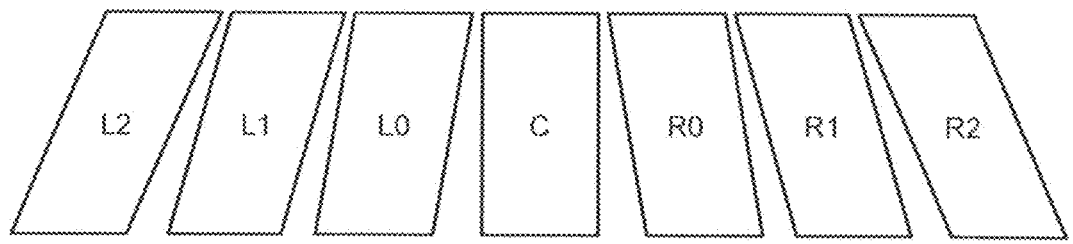

One example of a case in which the above-described methods are used when the number of directions is "7" will be described with reference to FIGS. 9A to 9D. In FIG. 9A, pieces of image data in seven directions that are generated by a frame sequence of deflection angles "$+\theta_2°, +\theta_1°, +\theta°, 0°, -\theta°, -\theta_1°,$ and $-\theta_2° (\theta_2>\theta_1>\theta)$" are denoted as "L2, L1, L0, C, R0, R1, and R2", respectively.

Figure 9B:
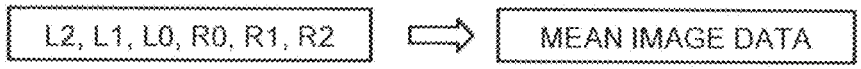

In this case, for example, the calculation unit 152 or the image generating unit 14 generates mean image data from the six pieces of image data "L2, L1, L0, R0, R1, and R2" as illustrated in FIG. 9B to calculate a coefficient distribution. In this case, the multiplication unit 153 multiplies "C" by the coefficient distribution.

Figure 9C:
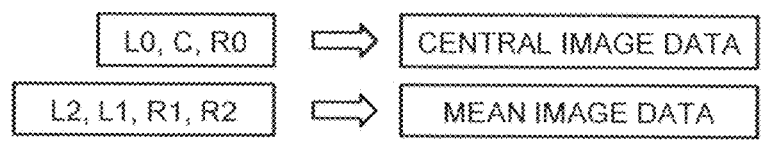

Alternatively, for example, the multiplication unit 153 or the image generating unit 14 performs weighted addition of "L0, C, and R0" to generate central image data as illustrated in FIG. 9C. Furthermore, for example, the calculation unit 152 or the image generating unit 14 generates mean image data from "L2, L1, R1, and R2" as illustrated in FIG. 9C to calculate a coefficient distribution.

Figure 9D:
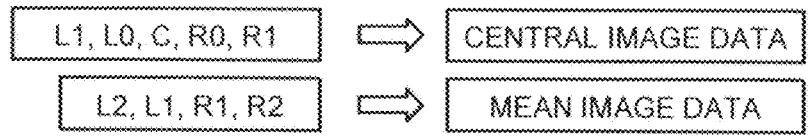

Alternatively, image data used for the mean image data may be used for the central image data. For example, the multiplication unit 153 or the image generating unit 14 performs weighted addition of "L1, L0, C, R0, and R1" to generate central image data as illustrated in FIG. 9D. Furthermore, for example, the calculation unit 152 or the image generating unit 14 generates mean image data from "L2, L1, R1, and R2" as illustrated in FIG. 9D to calculate a coefficient distribution. Even when these applications are performed, output image data can be obtained in which multiple reflections are reduced and also the lateral resolution and the sensitivity are maintained.

Regardless of whether a conventional method of performing a compounding process in frame sequence or the method according to the first embodiment in which multiplication processing is performed in frame sequence is used, the frame rate is not different from that in regular scanning of regular B-mode scanning. However, in both of the methods, there is a tendency that the responsivity of image change to movement of the ultrasonic probe 1, respiratory movement of the subject P, or the like decreases as the number of directions increases because of the influence of using frames the number of which corresponds to the number of directions for the processing. On the other hand, the effect of multiple reflection reduction becomes higher as the number of directions increases.

Accordingly, a trade-off occurs between the responsivity and the effect of multiple reflection reduction depending on the setting of the number of directions in the method according to the first embodiment. Thus, in the first embodiment, in order to allow the operator to select settings on "the number of directions in total" and "the number of directions used for generating mean image data and the number of directions used for generating central image data" as appropriate, candidate sets for these numbers of directions are preferably set in advance. In this case, the operator selects a desired setting from candidate sets displayed on a GUI, for example.

As described above, in the first embodiment, "weights (coefficients)" are calculated based on a group of pieces of oblique image data in which multiple reflections are reduced or pieces of oblique image data in which multiple reflections are reduced among a plurality of pieces of B-mode image data at different deflection angles that are generated by frame sequence. In the first embodiment, B-mode image data (front image data) at the "deflection angle: 0°" excellent in lateral resolution and sensitivity is used as central image data to be multiplied by the coefficient distribution to generate output image data. Alternatively, in the first embodiment, image data obtained by compounding a plurality of pieces of B-mode image data with front image data excellent in lateral resolution and sensitivity at the center is used as central image data to be multiplied by the coefficient distribution to generate output image data. Thus, in the first embodiment, a high-quality image can be obtained in which multiple reflections are reduced and also the lateral resolution and the sensitivity are maintained. It should be noted that, in the first embodiment, the above-described processing may be performed on signal values of B-mode data. In this case, ultrasound image data is generated by processing performed by the image generating unit 14 using data output by the multiplication unit 153.

Second Embodiment

In the first embodiment, a method has been described in which the effect of multiple reflection reduction and the maintenance of lateral resolution and sensitivity are achieved by performing multiplication processing in frame sequence instead of conventional methods of performing a compounding process in frame sequence. The concept of the processes described in the first embodiment can be used as an improved method of the conventional method of performing a space compounding process in rate sequence described with reference to FIG. 3B. In a second embodiment, with reference to FIGS. 10A to 11D, for example, a case will be described in which the effect of multiple reflection reduction and the maintenance of lateral resolution and sensitivity are achieved by performing multiplication processing in rate sequence. FIGS. 10A to 11D are diagrams illustrating the second embodiment.

An ultrasound diagnostic apparatus according to the second embodiment is configured similarly to the ultrasound diagnostic apparatus according to the first embodiment described with reference to FIG. 1. However, the data processing unit 15 according to the second embodiment performs the following processes.

Specifically, the acquisition unit 151 according to the second embodiment acquires received signals corresponding to a plurality of respective reception scan lines at different deflection angles for at least reception of an ultrasound wave. The acquisition unit 151 according to the second embodiment acquires received signals corresponding to the respective reception scan lines that are generated by ultrasound scanning in which deflection angles for ultrasound transmission and reception are changed between rates. For example, the acquisition unit 151 acquires a received-signal group including a plurality of received signals at different deflection angles that are generated by ultrasound scanning in which deflection angles for ultrasound transmission and reception are changed between rates. The calculation unit 152 according to the second embodiment then calculates coefficients corresponding to a plurality of respective depths on a reception scan line at a certain deflection angle, based on signal values or pixel values that are based on a received signal corresponding to at least one of reception scan lines at deflection angles except the certain deflection angle and that correspond to the respective depths. The coefficients corresponding to the respective depths constitute a coefficient distribution. For example, the calculation unit 152 uses received signals in at least one of deflection angles in directions except a certain direction among the received-signal group to calculate the coefficient distribution. For example, the calculation unit 152 calculates the above-described coefficients (the above-described coefficient distribution) based on a mean value between pieces of data to be processed. Alternatively, for example, the calculation unit 152 uses a function including arithmetic processing of exponentiating an input value to calculate the above-described coefficients (the above-described coefficient distribution). The multiplication unit 153 according to the second embodiment then multiplies, by the coefficients, signal values or pixel values that are based on a received signal corresponding to a reception scan line at a certain deflection angle or a signal obtained by compounding received signals corresponding to respective reception scan lines at a plurality of deflection angles including the certain deflection angle and that correspond to the respective depths on the reception scan line corresponding to the certain deflection angle. For example, the multiplication unit 153 multiplies, by the coefficient distribution, a received signal in the deflection angle in the certain direction or a signal obtained by compounding received signals in respective deflection angles in a plurality of directions including the certain direction among the received-signal group. For example, the multiplication unit 153 performs multiplication processing on data obtained by weighted addition as the above-described compounding process. The control unit 18 according to the second embodiment then causes the monitor 2 to display an image based on the signal values or the pixel values multiplied by the coefficients. For example, the control unit 18 causes the monitor 2 to display ultrasound image data based on the output data from the multiplication unit 153.

In rate sequence, when a signal of one reception scan line is obtained, ultrasound transmission and reception is performed a plurality of times at different deflection angles with the direction of this reception scan line at the center. In the second embodiment, the processes described in the first embodiment are applied to each received signal obtained by this transmission and reception performed plurality of times to obtain received signals in the direction of the reception scan line as final outputs.

Figure 10A:
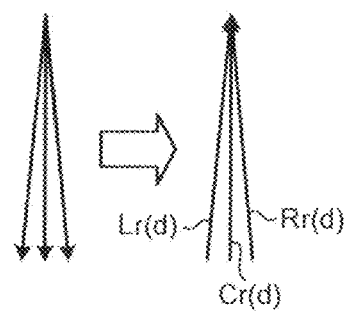

For example, under the control of the control unit 18, the transmitter-receiver unit 11 causes the ultrasonic probe 1 to perform ultrasound transmission and reception in three directions (deflection angles: 0°, +θ°, −θ°) on a rate-by-rate basis as illustrated in FIG. 10A. In this manner, three received signals at different deflection angles are obtained. The above-described certain direction herein is the direction of the deflection angle "0°", which is the direction of the reception scan line. The acquisition unit 151 then acquires these three received signals. "Lr(d)" and "Rr(d)" indicated in FIG. 10A are respectively a left-deflection received signal and a right-deflection received signal in which multiple reflection components are reduced by oblique transmission and reception. "Cr(d)" indicated in FIG. 10A is a received signal in the direction of the deflection angle "0°", and is a front signal (central signal) that can produce an image in which the lateral resolution and the sensitivity are high but multiple reflections may have occurred. "(d)" herein indicates the position of a received signal in the depth direction (reception scan line direction).

Figure 10B:
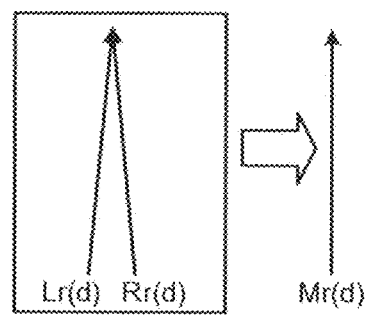

The following describes a case in which the calculation unit 152 calculates the coefficient distribution using "Lr(d)" and "Rr(d)" as objects to be processed and the multiplication unit 153 uses "Cr(d)" as an object to be multiplied. To begin with, the calculation unit 152 obtains "Mr(d)" that is a mean signal of "Lr(d)" and "Rr(d)" that are received signals in left deflection and right deflection, respectively, as illustrated in FIG. 10B. Specifically, the calculation unit 152 obtains "Mr(d)" according to Formula (4):

$$Mr(d)=(Lr(d)+Rr(d))/2 \qquad (4)$$

Figure 10C:
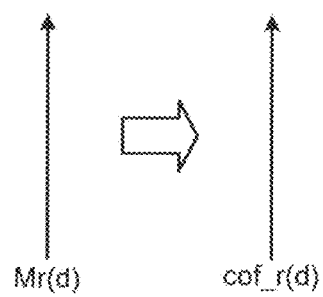

The calculation unit 152 then calculates a coefficient distribution "cof_r(d)" to be given for the central signal "Cr(d)" in the depth direction "d" from the mean signal "Mr(d)" as illustrated in FIG. 10C. Specifically, the calculation unit 152 calculates "cof_r(d)" according to Formula (5):

$$\left.\begin{array}{r} \mathrm{cof\_r}(d) = (Mr(d)/\beta)^{\alpha} \\ (\text{when } Mr(d) > \beta, \mathrm{cof\_r}(d) = 1.0) \end{array}\right\} \qquad (5)$$

In Formula (5) above, the value obtained by raising a quotient of Mr(d) divided by "β" to the "power of α" is defined as "cof_r(d)". In Formula (5) above, "cof_r(d)" is defined to be "1" when the quotient of Mr(d) divided by "β" is larger than "1". "α" and "β" herein are values that are set in advance as described in the first embodiment. Specifically, "β" means an upper limit of output received signals, and is set to be equal to or smaller than the maximum value "max" of the received signals. "β" is preferably set to be about 70% to 80% of "max". "α" is preferably set to be a value of about "¼ to ⅓".

Figure 10D:
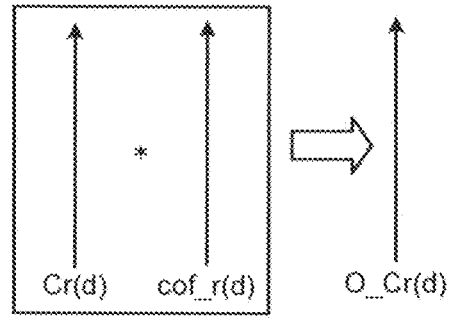

The multiplication unit 153 then multiplies the central signal "Cr(d)" by the coefficient distribution "cof_r(d)" to output an output received signal "O_Cr(d)" as illustrated in FIG. 10D. Specifically, the multiplication unit 153 performs arithmetic processing of Formula (6):

$$O\_Cr(d)=Cr(d)*cof\_r(d) \qquad (6)$$

Figure 10E:
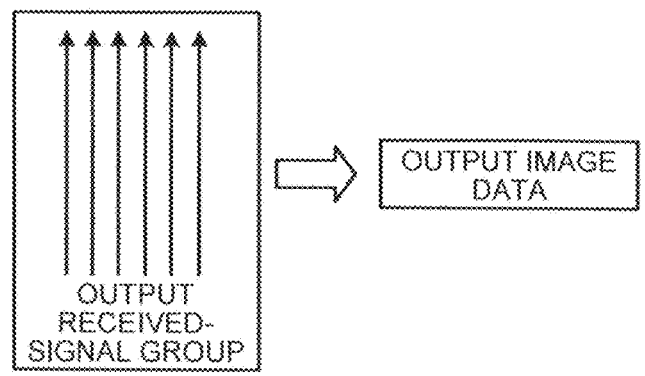

The data processing unit 15 performs the above-described processes on all reception scan lines to output output received signals for one frame. Under the control of the control unit 18, the image generating unit 14 generates output image data from the output received-signal group for one frame as illustrated in FIG. 10E. The monitor 2 then displays the output image data under the control of the control unit 18. This output image data becomes a high-quality image in which multiple reflections are reduced and also the lateral resolution and the sensitivity are maintained.

For the above-describe received signals "Lr(d), Rr(d), Cr(d)", any of RF signals or IQ signals including phase information, amplitude signals after phase detection, or logarithmically compressed data of the amplitude signals may be used. Any of these pieces of data can be used to define coefficients, and multiplication by the obtained coefficients can produce a high-quality image.

In the second embodiment also, one oblique received signal (e.g., "Lr(d)") may be used to calculate the coefficient distribution as described in the first embodiment. In the second embodiment also, the number of directions of deflection angles can be increased to five or seven as described in the first embodiment.

One example of processing performed when the number of directions is "7" will be described with reference to FIGS. 11A to 11D. In FIG. 11A, received signals in seven directions that are generated by rate sequence of deflection angles "+$\theta_2$°, +$\theta_1$°, +$\theta$°, 0°, −$\theta$°, −$\theta_1$°, and −$\theta_2$° ($\theta_2$>$\theta_1$>$\theta$)" are Denoted as "Lr2, Lr1, Lr0, Cr, Rr0, Rr1, and Rr2", respectively.

In this case, for example, the calculation unit 152 or the B-mode processing unit 12 generates a mean signal from the six received signals of "Lr2, Lr1, Lr0, Rr0, Rr1, and Rr2" as illustrated in FIG. 11B to calculate a coefficient distribution. In this case, the multiplication unit 153 multiplies "Cr" by the coefficient distribution.

Alternatively, for example, the multiplication unit 153 or the B-mode processing unit 12 performs weighted addition of "Lr0, Cr, Rr0" to generate a central signal as illustrated in FIG. 11C. Furthermore, for example, the calculation unit 152 or the B-mode processing unit 12 generates a mean signal from "Lr2, Lr1, Rr1, Rr2" as illustrated in FIG. 11C to calculate a coefficient distribution.

Alternatively, received signals used for the mean signal may be used for the central signal. For example, the multiplication unit 153 or the B-mode processing unit 12 performs weighted addition of "Lr1, Lr0, Cr, Rr0, Rr1" to generate a central signal as illustrated in FIG. 11D. Furthermore, for example, the calculation unit 152 or the B-mode processing unit 12 generates a mean signal from "Lr2, Lr1, Rr1, Rr2" as illustrated in FIG. 11D to calculate a coefficient distribution. Even when these application examples are performed, it is possible to obtain output received signals from which output image data can be generated in which multiple reflections are reduced and also the lateral resolution and the sensitivity are maintained.

When the application examples described with reference to FIGS. 11A to 11D are performed, in the second embodiment similarly to the first embodiment, in order for the operator to optionally select settings on "the number of directions in total" and "the number of directions used for generating a mean signal and the number of directions used for generating a central signal", candidate sets for these numbers of directions are preferably set in advance.

As described above, in the second embodiment, by performing multiplication processing with the coefficient distribution, the effect of multiple reflection reduction can be obtained while the lateral resolution and the sensitivity are being enhanced in comparison with conventional methods in which spatial compounding between rates is performed.

Third Embodiment

The concept of the multiplication processing described in the first embodiment and the second embodiment can be used as an improved method for the conventional methods of performing a space compounding process in parallel simultaneous reception described with reference to FIG. 3A. In a third embodiment, with reference to FIGS. 12A to 13D, for example, a case will be described in which the effect of multiple reflection reduction and the maintenance of lateral resolution and sensitivity are achieved by performing multiplication processing in parallel simultaneous reception. FIGS. 12A to 13D are diagrams illustrating the third embodiment.

An ultrasound diagnostic apparatus according to the third embodiment is configured similarly to the ultrasound diagnostic apparatus according to the first embodiment described with reference to FIG. 1. However, the data processing unit 15 according to the third embodiment performs the following processes.

Specifically, the acquisition unit 151 according to the third embodiment, similarly to the second embodiment, acquires received signals corresponding to a plurality of respective reception scan lines at different deflection angles for at least reception of an ultrasound wave. The acquisition unit 151 according to the third embodiment herein acquires received signals corresponding to the respective reception scan lines that are generated by ultrasound scanning in which a plurality of reflected waves at different deflection angles for ultrasound reception are received in response to each ultrasound transmission. For example, the acquisition unit 151 acquires a simultaneously-received-signal group including a plurality of simultaneously received signals at different deflection angles that are generated by ultrasound scanning in which reflected waves in a plurality of reception deflection angles are parallelly and simultaneously received in response to a transmitted ultrasound wave. The calculation unit 152 according to the third embodiment then, similarly to the second embodiment, calculates coefficients corresponding to a plurality of respective depths on a reception scan line at a certain deflection angle, based on signal values or pixel values that are based on a received signal corresponding to at least one of reception scan lines at a deflection angle other than the certain deflection angle and that correspond to the respective depths. The coefficients corresponding to the respective depths constitute a coefficient distribution. For example, the calculation unit 152 uses simultaneously received signals in at least one of deflection angles in directions except a certain direction among the simultaneously-received-signal group to calculate the coefficient distribution. For example, the calculation unit 152 calculates the above-described coefficients (the above-described coefficient distribution) based on a mean value between pieces of data to be processed. Alternatively, for example, the calculation unit 152 uses a function including arithmetic processing of exponentiating an input value to calculate the above-described coefficients (the above-described coefficient distribution). The multiplication unit 153 according to the third embodiment then, similarly to the second embodiment, multiplies, by the coefficients, signal values or pixel values that are based on a received signal corresponding to a reception scan line at a certain deflection angle or a signal obtained by compounding received signals corresponding to respective reception scan lines at a plurality of deflection angles including the certain deflection angle and that correspond to the respective depths on the reception scan line corresponding to the certain deflection angle. For example, the multiplication unit 153 multiplies, by the coefficient distribution, a simultaneously received signal in the deflection angle in the certain direction or a signal obtained by compounding simultaneously received signals in respective deflection angles in a plurality of directions including the certain direction among the simultaneously-received-signal group. For example, the multiplication unit 153 performs multiplication processing on data obtained by weighted addition as the above-described compounding process. The control unit 18 according to the third embodiment then causes the monitor 2 to display an image based on the signal values or the pixel values multiplied by the coefficients. For example, the control unit 18 causes the monitor 2 to display ultrasound image data based on the output data from the multiplication unit 153.

In parallel simultaneous reception, when a signal of one reception scan line is obtained, a plurality of received signals (simultaneously received signals) at different deflection angles are simultaneously acquired with the direction of this reception scan line at the center. In the third embodiment, the processes described in the second embodiment are applied to these simultaneously received signals to obtain signals in the direction of the reception scan line as final outputs.

Figure 12A:
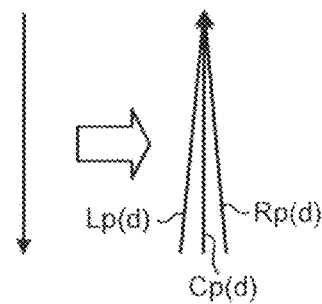

For example, under the control of the transmitter-receiver unit 11 via the control unit 18, the ultrasonic probe 1 transmits an ultrasound beam in the deflection angle "0°" and simultaneously receives reflected waves in three directions (deflection angles: 0°, +θ°, −θ°) as illustrated in FIG. 12A. In this manner, three simultaneously received signals at different deflection angles are obtained. The above-described certain direction herein is the direction of the deflection angle "0°", which is the direction of the reception scan line. The acquisition unit 151 then acquires these three simultaneously received signals. "Lp(d)" and "Rp(d)" indicated in FIG. 12A are respectively a left-deflection simultaneously received signal and a right-deflection simultaneously received signal in which multiple reflection components are reduced by oblique transmission and reception. "Cp(d)" indicated in FIG. 12A is a simultaneously received signal in the direction of the deflection angle "0°", and is a front signal (central signal) that can produce an image in which the lateral resolution and the sensitivity are high but multiple reflections may have occurred. "(d)" herein indicates the position of a simultaneously received signal in the depth direction (reception scan line direction).

For the above-described simultaneously received signals "Lp(d), Rp(d), Cp(d)", similarly to the second embodiment, any of RF signals or IQ signals including phase information, amplitude signals after phase detection, or logarithmically compressed data of the amplitude signals may be used. Any of these pieces of data can be used to define coefficients described later.

Figure 12B:
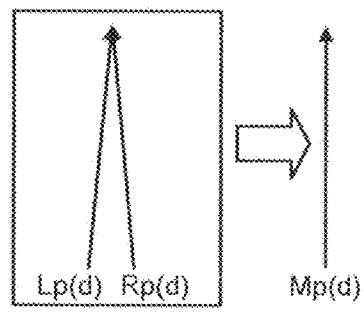

The following describes a case in which the calculation unit 152 calculates the coefficient distribution using "Lp(d)" and "Rp(d)" as objects to be processed and the multiplication unit 153 uses "Cp(d)" as an object to be multiplied. To begin with, the calculation unit 152 obtains a mean signal "Mp(d)" of "Lp(d)" and "Rp(d)" that are simultaneously received signals in left deflection and right deflection, respectively, as illustrated in FIG. 12B. Specifically, the calculation unit 152 obtains "Mp(d)" according to Formula (7):

$$Mp(d)=(Lp(d)+Rp(d))/2 \qquad (7)$$

Figure 12C:
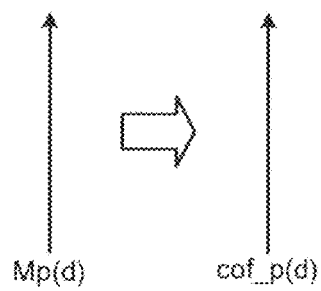

The calculation unit 152 then calculates a coefficient distribution "cof_p(d)" to be given for the central signal "Cp(d)" in the depth direction "d" from the mean signal "Mp(d)" as illustrated in FIG. 12C. Specifically, the calculation unit 152 calculates "cof_p(d)" according to Formula (8):

$$\left.\begin{array}{r}\text{cof\_p}(d) = (Mp(d)/\beta)^{\alpha} \\ (\text{when } Mp(d) > \beta, \text{cof\_p}(d) = 1.0)\end{array}\right\} \qquad (8)$$

In Formula (8) above, the value obtained by raising a quotient of Mp(d) divided by "β" to the "power of α" is defined as "cof_p(d)". In Formula (8) above, "cof_p(d)" is defined to be "1" when the quotient of Mp(d) divided by "β" is larger than "1". "α" and "β" herein are values that are set in advance as described in the first embodiment and the second embodiment. Specifically, "β" means an upper limit of output simultaneously received signals, and is set to be equal to or smaller than the maximum value "max" of the simultaneously received signals. "β" is preferably set to be about 70% to 80% of "max". "α" is preferably set to be a value of about "¼ to ⅓".

Figure 12D:
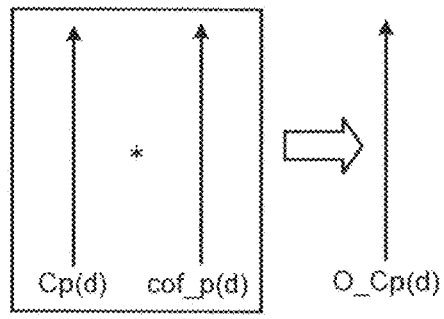

The multiplication unit 153 then multiplies the central signal "Cp(d)" by the coefficient distribution "cof_p(d)" to output an output received signal "O_Cp(d)" as illustrated in FIG. 12D. Specifically, the multiplication unit 153 performs arithmetic processing of Formula (9):

$$O\_Cp(d)=Cp(d)*\text{cof\_}p(d) \qquad (9)$$

Figure 12E:
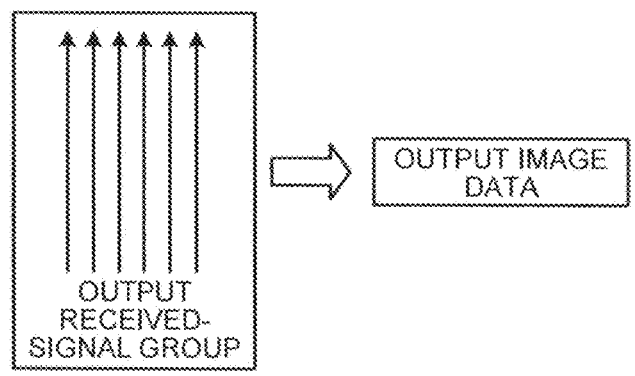

The data processing unit 15 performs the above-described processes on all reception scan lines to output output received signals for one frame. Under the control of the control unit 18, the image generating unit 14 generates output image data from the output received-signal group for one frame as illustrated in FIG. 12E. The monitor 2 then displays the output image data under the control of the control unit 18. This output image data becomes a high-quality image in which multiple reflections are reduced and also the lateral resolution and the sensitivity are maintained.

In the third embodiment also, one oblique simultaneously received signal (e.g., "Lp(d)") may be used to calculate the coefficient distribution as described in the second embodiment. In the third embodiment also, the number of directions of deflection angles can be increased to five or seven as described in the first embodiment and the second embodiment.

One example of processing performed when the number of directions is "7" will be described with reference to FIGS. 13A to 13D. In FIG. 13A, simultaneously received signals in seven directions that are generated by rate sequence of deflection angles "+θ$_2$°, +θ$_1$°, +θ°, 0°, −θ°, −θ$_1$°, and −θ$_2$° (θ$_2$>θ$_1$>θ)" are denoted as "Lp2, Lp1, Lp0, Cp, Rp0, Rp1, and Rp2", respectively.

In this case, for example, the calculation unit 152 or the B-mode processing unit 12 generates a mean signal from the six received signals of "Lp2, Lp1, Lp0, Rp0, Rp1, and Rp2" as illustrated in FIG. 13B to calculate a coefficient distribution. In this case, the multiplication unit 153 multiplies "Cp" by the coefficient distribution.

Alternatively, for example, the multiplication unit 153 or the B-mode processing unit 12 performs weighted addition of "Lp0, Cp, Rp0" to generate a central signal as illustrated in FIG. 13C. Furthermore, for example, the calculation unit 152 or the B-mode processing unit 12 generates a mean signal from "Lp2, Lp1, Rp1, and Rp2" as illustrated in FIG. 13C to calculate a coefficient distribution.

Alternatively, simultaneously received signals used for the mean signal may be used for the central signal. For example, the multiplication unit 153 or the B-mode processing unit 12 performs weighted addition of "Lp1, Lp0, Cp, Rp0, and Rp1" to generate a central signal as illustrated in FIG. 13D. Furthermore, for example, the calculation unit 152 or the B-mode processing unit 12 generates a mean signal from "Lp2, Lp1, Rp1, Rp2" as illustrated in FIG. 13D to calculate a coefficient distribution. Even when these application examples are performed, it is possible to obtain output received signals from which output image data can be generated in which multiple reflections are reduced and also the lateral resolution and the sensitivity are maintained.

When the application examples described with reference to FIGS. 13A to 13D are performed, in the third embodiment similarly to the first embodiment and the second embodiment, in order for the operator to optionally select settings on "the number of directions in total" and "the number of directions used for generating a mean signal and the number of directions used for generating a central signal", candidate sets for these numbers of directions are preferably set in advance.

As described above, in the third embodiment, by performing multiplication processing with the coefficient distribution, the effect of multiple reflection reduction can be obtained while the lateral resolution and the sensitivity are being enhanced in comparison with conventional methods in which spatial compounding is performed in parallel simultaneous reception.

Fourth Embodiment

In a fourth embodiment, a case will be described in which the processes described in the first to the third embodiments are performed in combination.

Specifically, in a scan mode (hereinafter, first scan mode) of the frame sequence described in the first embodiment, a scan mode (hereinafter, second scan mode) of the rate sequence described in the second embodiment, and a scan mode (hereinafter, third scan mode) of the parallel simultaneous reception described in the third embodiment, settings of deflection angles can be set independently of each other. Thus, operations described in the first to the third embodiments can be used together in optional combination. This enables the achievement of the effect of multiple reflection reduction and the maintenance of lateral resolution and sensitivity.

When at least two of the three types of scan modes are used together, multiplication processing with coefficients (coefficient distribution) may be performed in at least one of the scan modes and a conventional method (compounding process) may be performed in the remaining scan modes. This also enables the achievement of the effect of multiple reflection reduction and the maintenance of lateral resolution and sensitivity.

In view of this, an ultrasound diagnostic apparatus according to the fourth embodiment is configured as follows. The acquisition unit 151 according to the fourth embodiment has a function of acquiring the image data group (pieces of ultrasound image data at different deflection angles) described in the first embodiment, the received-signal group (received signals corresponding to the respective reception scan lines at different deflection angles) described in the second embodiment, and the simultaneously-received-signal group (received signals corresponding to the respective reception scan lines at different deflection angles) described in the third embodiment.

For example, the calculation unit 152 according to the fourth embodiment has a function of calculating the coefficients (coefficient distribution) described in the first embodiment, a function of calculating the coefficients (coefficient distribution) described in the second embodiment, and a function of calculating the coefficients (coefficient distribution) described in the third embodiment. For example, the multiplication unit 153 according to the fourth embodiment has the multiplication function described in the first embodiment, the multiplication function described in the second embodiment, and the multiplication function described in the third embodiment.

When at least two of the first scan mode, the second scan mode, and the third scan mode are used together, the control unit 18 according to the fourth embodiment performs control to perform multiplication processing with a coefficient distribution corresponding to at least one data group in a plurality of data groups obtained by a scan mode performed. When there is a data group on which multiplication processing is not performed, the control unit 18 according to the fourth embodiment performs control to perform a compounding process on the data group. The control unit 18 according to the fourth embodiment then causes the monitor 2 to display ultrasound image data that is an image output by these control processes.

The following describes processes performed in the fourth embodiment with reference to FIGS. 14 to 21. FIGS. 14 to 21 are diagrams illustrating the fourth embodiment. Selection of combinations of scan modes and processes in each scan mode described below is performed in various manners. For example, the operator may determine a setting, or the operator may select a setting from a plurality of presets that are initially set.

Figure 14:
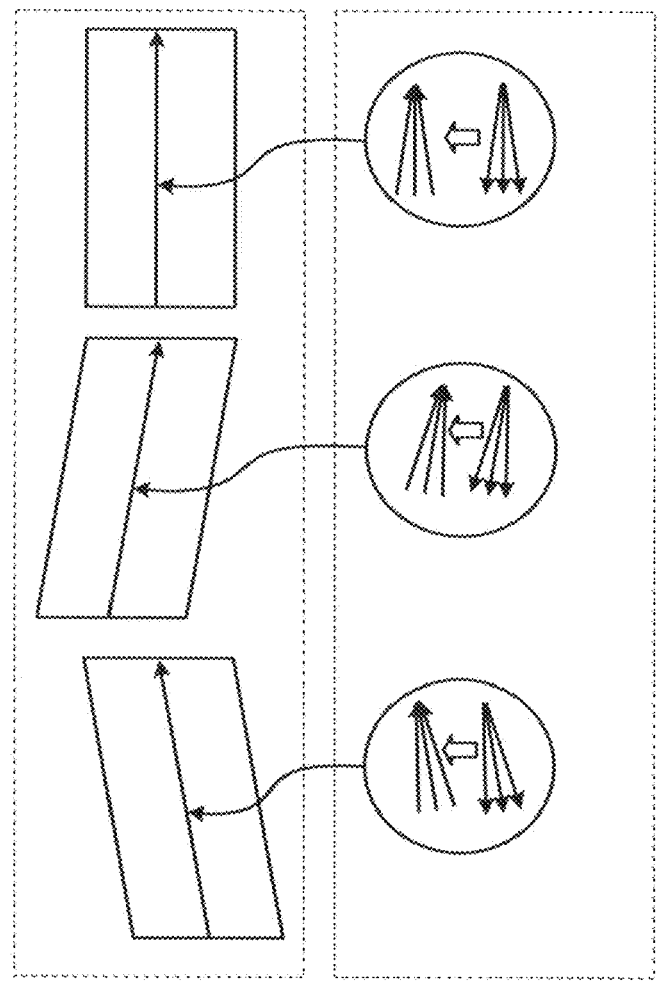

A case of using together the first scan mode and the second scan mode will be described with reference to FIGS. 14 and 15. FIG. 14 illustrates a case in which three directions are set as deflection angles for the whole image data in the first scan mode and, in the second scan mode, when a received signal is obtained from one reception scan line in image data of each of the directions, three directions are set for transmission and reception.

Figures 15, 16:
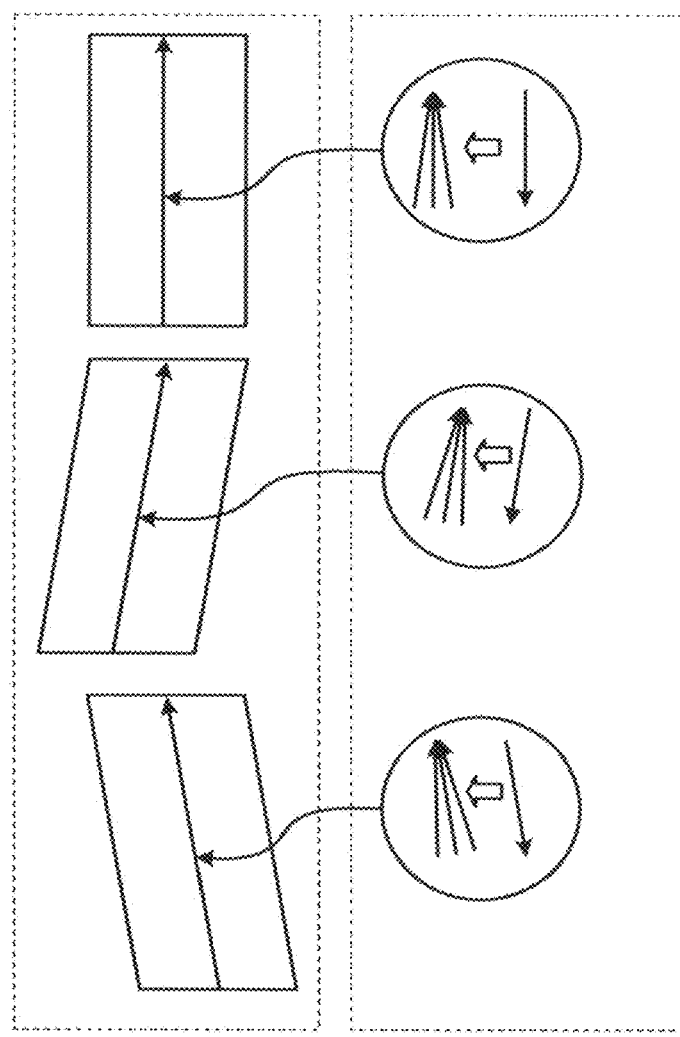

In this case, processes in each scan mode can be selected from three types of combinations illustrated in FIG. 15. In FIG. 15, "M" denotes multiplication processing with the coefficient distribution, and "C" denotes a conventional compounding process. Specifically, when the first scan mode and the second scan mode are used together, as illustrated in FIG. 15, there are three patterns that are cases of performing the process in "first scan mode: M, second scan mode: M", performing the process in "first scan mode: M, second scan mode: C", and performing the process in "first scan mode: C, second scan mode: M".

Figures 17, 18:
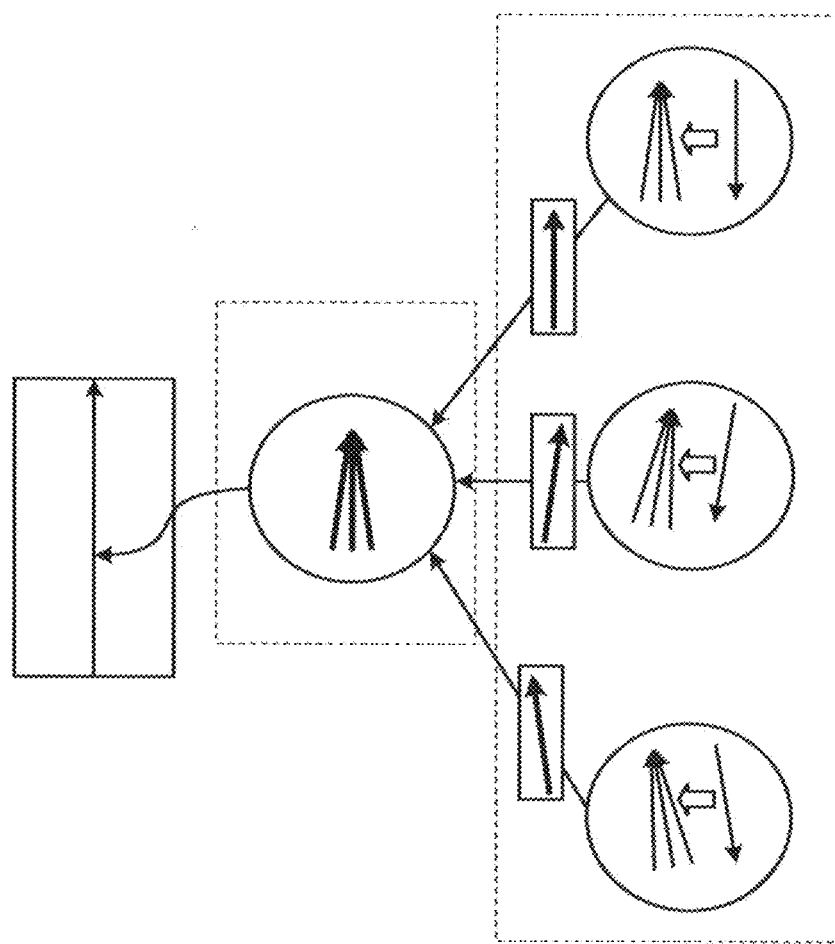

The following describes a case in which the first scan mode and the third scan mode are used together, with reference to FIGS. 16 and 17. FIG. 16 illustrates a case in which three directions are set as deflection angles for the whole image data in the first scan mode and, in the third scan mode, when a received signal is obtained from one reception scan line in image data of each of the directions, three directions are set for simultaneous reception in response to a transmission beam in one direction.

In this case, processes in each scan mode can be selected from three types of combinations illustrated in FIG. 17. Specifically, when the first scan mode and the third scan mode are used together, as illustrated in FIG. 17, there are three patterns that are cases of performing the process in "first scan mode: M, third scan mode: M", performing the process in "first scan mode: M, third scan mode: C", and performing the process in "first scan mode: C, third scan mode: M".

The following describes a case in which the second scan mode and the third scan mode are used together, with reference to FIGS. 18 and 19. FIG. 18 illustrates a case in which three directions are set for transmission and reception when a received signal is obtained from one reception scan line in front image data of "0°" in the second scan mode, and the third scan mode is set to obtain simultaneously received signals that, with each direction of these three directions for transmission and reception at the center, are deflected into three directions.

In this case, processes in each scan mode can be selected from three types of combinations illustrated in FIG. 19. Specifically, when the second scan mode and the third scan mode are used together, as illustrated in FIG. 19, there are three patterns that are cases of performing the process in "second scan mode: M, third scan mode: M", performing the process in "second scan mode: M, third scan mode: C", and performing the process in "second scan mode: C, third scan mode: M".

Figure 20:
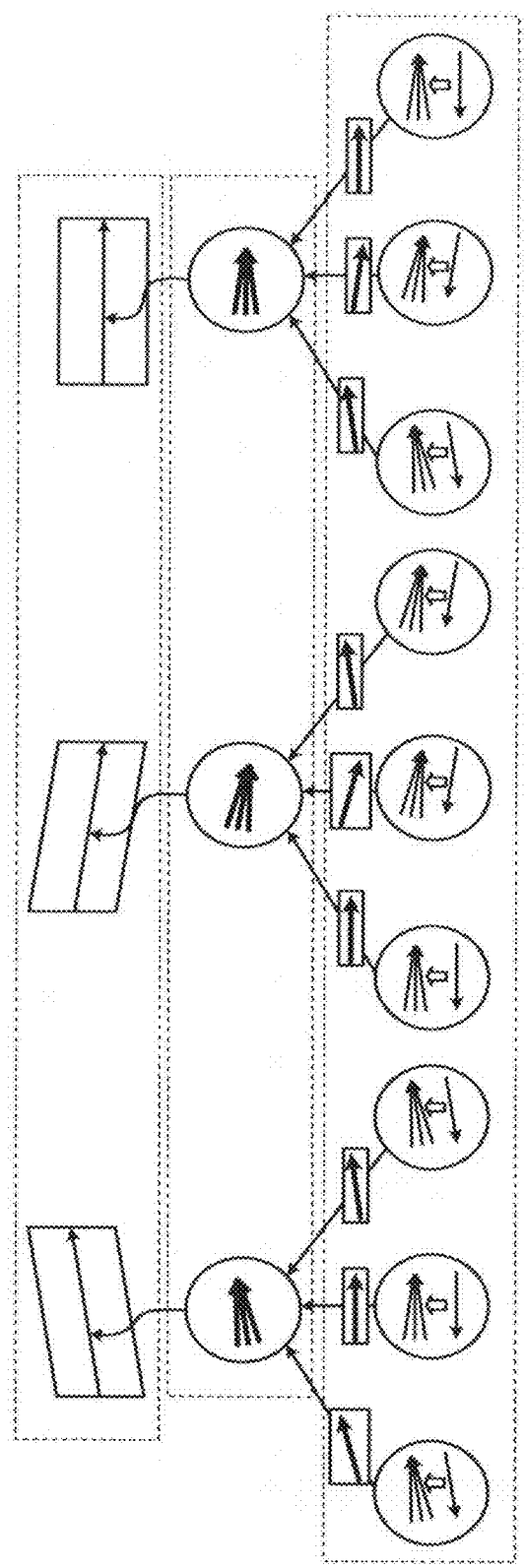
Figures 21, 22:
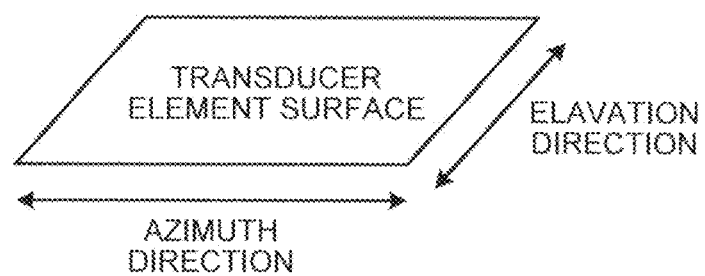

The following describes a case in which the first scan mode, the second scan mode, and the third scan mode are used together, with reference to FIGS. 20 and 21. FIG. 20 illustrates a case in which three directions are set as deflection angles for the whole image data in the first scan mode and, in the second scan mode, when a received signal is obtained from one reception scan line in image data of each of the directions, three directions are set for transmission and reception. FIG. 20 further illustrates in the case that the third scan mode is set to obtain simultaneously received signals that, with each direction of these three directions for transmission and reception in the second scan mode at the center, are deflected into three directions.

In this case, processes in each scan mode can be selected from seven types of combinations illustrated in FIG. 21. Specifically, when the first scan mode, the second scan mode, and the third scan mode are used together, as illustrated in FIG. 21, there are cases of performing the process in "first scan mode: M, second scan mode: M, third scan mode: M", performing the process in "first scan mode: M, second scan mode: M, third scan mode: C", performing the process in "first scan mode: M, second scan mode: C, third scan mode: M", and performing the process in "first scan mode: C, second scan mode: M, third scan mode: M". In addition, when the first scan mode, the second scan mode, and the third scan mode are used together, as illustrated in FIG. 21, there are cases of performing the process in "first scan mode: M, second scan mode: C, third scan mode: C", performing the process in "first scan mode: C, second scan mode: M, third scan mode: C", and performing the process in "first scan mode: C, second scan mode: C, third scan mode: M".

Performing any of the processes illustrated in FIGS. 15, 17, 19, and 20 can also produce a high-quality image in which multiple reflections are reduced and also the lateral resolution and the sensitivity are maintained. It should be noted that the foregoing describes merely examples. For example, in the case in which the first scan mode, the second scan mode, and the third scan mode are used together, seven directions may be set as deflection angles for the whole image data in the first scan mode and, in the second scan mode, when a received signal is obtained from one reception scan line in image data in each of the directions, five directions for transmission and reception may be set. In this case, the third scan mode may be further set to obtain simultaneously received signals that, with each direction of these five directions for transmission and reception in the second scan mode at the center, are deflected into three directions.

According to the fourth embodiment described above, a degree of flexibility in an image-quality setting method using a coefficient distribution with multiplication processing combined can be increased depending on an image-quality request that the operator desires. Specifically, the fourth embodiment allows the operator to select, from the setting candidate sets, setting of image quality that is determined by which of the responsivity, the frame rate, the spatial resolution (lateral resolution), the sensitivity, and the multiple reflection components priority is placed on, in view of the balance therebetween.

Fifth Embodiment

In the first to the fourth embodiments, cases have been described in which mean values in a plurality of directions are used with respect to image signals with deflection or received signals with deflection when a coefficient distribution is calculated. In a fifth embodiment, with respect to signal components and noise components such as multiple reflection components, another configuration example that exerts the same effect as the mean values will be described below with reference to formulae, for example.

As described in the first embodiment, like a scattered signal (real signal), if a signal level does not change in a certain region even when seen from either the right or the left, correlation between pieces of data is high. In contrast, like multiple reflection components, if the appearance position changes depending on the respective deflections to the right and to the left, correlation in signal level at a certain region is low between right deflection signals and left deflection signals.

Accordingly, the calculation unit 152 according to the fifth embodiment, as a process directly using these characteristics, calculates coefficients (coefficient distribution) based on local cross-correlation coefficient values between pieces of data to be processed. Alternatively, the calculation unit 152 according to the fifth embodiment, as a process indirectly using these characteristics, calculates coefficients (coefficient distribution) based on difference values between pieces of data to be processed.

The following describes a case of calculating a coefficient distribution "cof(x,y)" based on the cross-correlation coefficient values and a case of calculating a coefficient distribution "cof(x,y) based on difference values, using the left-deflection image data and the right-deflection image data described in the first embodiment. The content described below can be applied to the second, the third, or the fourth embodiment by using data to be handled as received signals.

A calculation example of the coefficient distribution based on cross-correlation coefficient values will be described. For example, the calculation unit 152 calculates cross-correlation coefficients "corr(x,y)" between "L(x,y)" and "R(x,y)" in the overlapping area illustrated in FIG. 4B, and calculates a coefficient distribution "cof(x,y)" from "corr(x,y)" according to Formula (10):

$$\left. \begin{array}{l} cof(x, y) = (\mathrm{corr}(x, y)/\beta)^\alpha \\ (\text{when } \mathrm{corr}(x, y) > \beta, cof(x, y) = 1.0) \end{array} \right\} \quad (10)$$

In Formula (10) above, the value obtained by raising a quotient of "corr(x,y)" divided by "β" to the "power of α" is defined as "cof(x,y)". In Formula (10) above, "cof(x,y)" is defined to be "1" when the quotient of "corr(x,y)" divided by "β" is larger than "1". "α" and "β" herein are set values described in the first embodiment. Formula (10) above means that the cross-correlation coefficient value itself is used as a coefficient value on the assumption that "α=1.0, β=1.0".

In a case that the number of directions of lateral deflection is equal to or larger than three, when priority is given to increasing the effect of multiple reflection reduction, the calculation unit 152 calculates cross-correlation coefficients between all pairs of signals that can be combined. The calculation unit 152 then substitutes a minimum value "min_corr(x,y)" of a plurality of cross-correlation coefficients thus calculated for "corr(x,y)" in Formula (10).

In the case that the number of directions of lateral deflection is equal to or larger than three, when priority is given to keeping a balance between the maintenance of signal components and the effect of multiple reflection reduction, the calculation unit 152 substitutes an average value "ave_corr(x,y)" of the cross-correlation coefficients calculated for "corr(x,y)" in Formula (10). The operator can determine which of these two methods to be selected.

Because the cross-correlation coefficients herein can be obtained by giving a certain degree of expansion "(±δx, ±δy)" with "(x,y)" at the center, the spatial stability with respect to correlation estimation is relatively high. However, because expansion in the same degree as "(±δx,±δy)" is generated also in "cof(x,y)" that is obtained with the cross-correlation coefficients, it is sometimes difficult to maintain the spatial resolution with respect to coefficient control.

In contrast, in a configuration of using difference values as a process indirectly using the above-described characteristics, the spatial resolution can be increased more than the case of using cross-correlation coefficients. For example, the calculation unit 152 calculates a difference value "D(x,y)" between signals in "L(x,y)" and "R(x,y)" according to Formula (11) below in the overlapping area illustrated in FIG. 4B. In areas excluding the overlapping area, "L(x,y)" or "R(x,y)" is "D(x,y)".

$$D(x,y) = sqrt((L(x,y) - R((x,y))^2) \qquad (11)$$

In this configuration, the coefficient distribution "cof(x, y)" is defined by using the fact that difference values are small when the correlation between "L(x,y)" and "R(x,y)" being the left and the right deflection signals is high, and the difference values are large when the correlation is low. In this configuration, the calculation unit 152 calculates "sub(x,y)" according to Formula (12) below from the maximum value "max" of the input signals described above and "D(x,y)". The value of "sub(x,y)" obtained by Formula (12) below is large when the correlation is high, and the value is small when the correlation is low.

$$sub(x,y) = max - D(x,y) \qquad (12)$$

The calculation unit 152 then calculates a coefficient distribution "cof(x,y)" from "sub(x,y) according to Formula (13):

$$cof(x, y) = (sub(x, y)/\beta)^\alpha \\ (\text{when } sub(x, y) > \beta, cof(x, y) = 1.0) \qquad (13)$$

In Formula (13) above, the value obtained by raising a quotient of "sub(x,y)" divided by "β" to the "power of α" is defined as "cof(x,y)". In Formula (13) above, "cof(x,y)" is defined to be "1" when the quotient of "sub(x,y)" divided by "β" is larger than "1". "α" and "β" herein are the same set values as described above.

Furthermore, in the fifth embodiment, the coefficient distribution may be calculated by using the mean values together with the difference values. In this case, the calculation unit 152 according to the fifth embodiment calculates coefficients (coefficient distribution) based on a difference value between pieces of data to be processed and mean values between the pieces of data to be processed. For example, the calculation unit 152 calculates "sub(x,y)" according to Formula (14) below using "max", "D(x,y)", and "M(x,y)". The calculation unit 152 then substitutes "sub(x,y)" obtained by Formula (14) below for "sub(x,y)" in Formula (13) to calculate a coefficient distribution "cof(x, y)".

$$sub(x, y) = max - D(x, y)/M(x, y) \quad (M(x, y) \neq 0) \qquad (14)$$
$$= 0.0 \qquad (M(x, y) = 0)$$

In Formula (14) above, "sub(x,y)" is defined to be "0.0" when "M(x,y)" is "0", and the magnitude of the difference value "D(x,y)" is normalized with the mean value "M(x,y)" when "M(x,y)" is not "0". In the fifth embodiment, using the definition of Formula (14) can automatically provide an appropriate coefficient depending on the level of an input signal.

In the configuration of using difference values, and also in the configuration of using difference values and mean values, in the case that the number of directions of lateral deflection is equal to or larger than three, when priority is given to increasing the effect of multiple reflection reduction, the calculation unit 152 calculates difference values between all pairs of signals that can be combined. The calculation unit 152 then substitutes the maximum value "max_D(x,y)" of a plurality of difference values thus calculated for "D(x,y)" in Formula (12) or Formula (14) to calculate "sub(x,y)".

Alternatively, in the case that the number of directions of lateral deflection is equal to or larger than three, when priority is given to keeping a balance between the maintenance of signal components and the effect of multiple reflection reduction, the calculation unit 152 substitutes an average value "ave_D(x,y)" of the difference values calculated for "D(x,y)" in Formula (12) or Formula (14) to calculate "sub(x,y)". The operator can determine which of these two methods to be selected.

It should be noted that, in all of the configuration of using cross-correlation coefficient values, the configuration of using difference values, and the configuration of using difference values and mean values, when lateral deflection signals do not overlap, a coefficient generation method (see the first to the third embodiments) is preferably used in which mean values of signals in at least one direction of the lateral deflection signals are used.

By the coefficient generation method described in the fifth embodiment also, a high-quality image can be obtained in which multiple reflections are reduced and also the lateral resolution and the sensitivity are maintained.

The ultrasound imaging methods described in the first to the fifth embodiments can be applied to not only a case of imaging general B-mode image data but also, as a modification, a case of performing harmonic imaging such as tissue harmonic imaging (THI) or contrast harmonic imaging (CHI). Furthermore, the ultrasound imaging methods described in the first to the fifth embodiments can be applied to a case of using together frequency compounding, which is a method of compounding image signals in a plurality of frequency bands, in addition to the above-described spatial compounding process.

Furthermore, the ultrasound imaging methods described in the first to the fifth embodiments can be applied to not only a case of imaging two-dimensional ultrasound image data but also a case of imaging volume data as a modification.

For example, when a mechanical four-dimensional probe is used as the ultrasonic probe 1, volume data is generated by compounding a plurality of tomographic views that are obtained by mechanically swinging the transducer element group. In this case, setting a plurality of directions at different deflection angles in each of the tomographic views can provide high-quality volume data in which multiple reflections are reduced and also the lateral resolution and the sensitivity are maintained.

Furthermore, for example, when a two-dimensional array probe that performs three-dimensional real-time scanning is used as the ultrasonic probe 1, the ultrasound imaging methods described in the first to the fifth embodiments can be used. FIG. 22 is a diagram illustrating a modification. In this case, as illustrated in FIG. 22, for example, on an array surface (transducer element surface) of a two-dimensional array transducer element, by two-dimensionally setting a plurality of directions at different deflection angles in the azimuth direction and also in the elevation direction, high-quality volume data can be obtained in which multiple reflections are reduced and also the lateral resolution and the sensitivity are maintained. Two-dimensional image data generated from this volume data also becomes a high-quality image in which multiple reflections are reduced and also the lateral resolution and the sensitivity are maintained.

Among the processes described in the first to the fifth embodiments and the modifications, all or part of processes described as automatically performed processes can be manually performed, and all or part of processes described as manually performed processes can be automatically performed by a known method. In addition, information including processing procedures, control procedures, specific names, various types of data or parameters may be optionally changed except as otherwise specified.

The components of each device illustrated are functionally conceptual, and are not necessarily required to be physically configured as illustrated in the drawings. In other words, concrete forms of distribution and integration of the units are not limited to those illustrated in the drawings, and all or part of the units can be configured to be functionally or physically distributed and integrated in an arbitrary unit depending on various loads and conditions in use. Furthermore, all or an arbitrary part of the processing functions performed by the respective units can be implemented by a CPU and a computer program to be executed by the CPU, or can be implemented as hardware by wired logic.

The ultrasound imaging methods described in the first to the fifth embodiments and the modifications described above can be achieved by executing control programs prepared in advance in a computer such as a personal computer or a work station. The ultrasound imaging methods can be distributed via a network such as the Internet. Furthermore, the ultrasound imaging methods can be stored in a computer-readable recording medium such as a hard disc, a flexible disc (FD), a CD-ROM, an MO, and a DVD, and read out from the recording medium by the computer.

As described in the foregoing, according to the first to the fifth embodiments and the modifications, a high-quality image can be obtained in which multiple reflections are reduced and also the lateral resolution and the sensitivity are maintained.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
processing circuitry configured to
acquire a plurality of pieces of ultrasound image data, each of the plurality of pieces of ultrasound image data being acquired at a different deflection angle, of a plurality of different deflection angles, for both of ultrasound transmission and reception, the plurality of different deflection angles including a first deflection angle;
calculate coefficients, each coefficient corresponding to a spatial position and being separately calculated for each spatial position, of a plurality of spatial positions in a first piece of ultrasound image data, of the acquired plurality of pieces of ultrasound image data, acquired at the first deflection angle, each of the coefficients being calculated based on a signal value or a pixel value at a corresponding spatial position, of the plurality of spatial positions, in at least one of the acquired plurality of pieces of ultrasound image data acquired at a deflection angle of the plurality of different deflection angles other than the first deflection angle, wherein the first piece of ultrasound image data acquired at the first deflection angle is not used for calculating the coefficients;
generate an output image by multiplying, by the coefficients, signal values or pixel values corresponding to the plurality of spatial positions in the first piece of ultrasound image data acquired at the first deflection angle, or signal values or pixel values corresponding to the plurality of spatial positions in a piece of image data that is obtained by compounding the plurality of pieces of ultrasound image data acquired at the plurality of different deflection angles including the first deflection angle; and
cause a display to display the output image,
wherein an absolute value of each of the plurality of different deflection angles is larger than the first deflection angle.

2. The ultrasound diagnostic apparatus according to claim 1, wherein the processing circuitry is further configured to acquire the plurality of pieces of ultrasound image data at the plurality of different deflection angles, each piece of ultrasound image data corresponding to a frame of a plurality of frames, and each frame corresponding to one of the plurality of different deflection angles.

3. The ultrasound diagnostic apparatus according to claim 1, wherein the processing circuitry is further configured to calculate the coefficients based on mean values calculated from the plurality of pieces of ultrasound image data.

4. The ultrasound diagnostic apparatus according to claim 3, wherein the processing circuitry is further configured to calculate the coefficients using an exponentiation function.

5. The ultrasound diagnostic apparatus according to claim 1, wherein the processing circuitry is further configured to calculate the coefficients based on local cross-correlation coefficient values calculated from the plurality of pieces of ultrasound image data, based on difference values calculated from the plurality of pieces of ultrasound image data, or based on the calculated difference values and mean values calculated from the plurality of pieces of ultrasound image data.

6. The ultrasound diagnostic apparatus according to claim 5, wherein the processing circuitry is further configured to calculate the coefficients using an exponentiation function.

7. The ultrasound diagnostic apparatus according to claim 1, wherein the compounding comprises weighted addition.

8. The ultrasound diagnostic apparatus according to claim 1, wherein the absolute value of each of the plurality of different deflection angles, at which the processing circuitry acquires the plurality of pieces of ultrasound image data, is larger than the first deflection angle, with an orientation that is perpendicular to an array direction of transducer elements, which is defined as an orientation of zero degrees.

9. An ultrasound diagnostic apparatus, comprising:
processing circuitry configured to
acquire received signals, each of the received signals corresponding to one of a plurality of reception scan lines, and each of the reception scan lines corresponding to a different deflection angle of a plurality of different deflection angles used for reception of a corresponding ultrasound wave, the plurality of different deflection angles including a first deflection angle;
calculate coefficients, each coefficient corresponding to one depth of a plurality of depths on a first reception scan line corresponding to the first deflection angle, the coefficient being calculated based on a first signal value or a first pixel value at the one depth and being derived from the received signals corresponding to at least one reception scan line, each coefficient being separately calculated for each one depth, of the plurality of reception scan lines, having a deflection angle other than the first deflection angle;
generate an output image by multiplying, by the coefficients, second signal values or second pixel values acquired from the received signals corresponding to the first reception scan line or signals obtained by compounding the received signals corresponding to the reception scan lines at the plurality of deflection angles including the first deflection angle, the second signal values or the second pixel values having values at the plurality of depths on the first reception scan line; and
cause a display to display the output image,
wherein signal values or pixel values acquired at the first deflection angle are not used for calculating the coefficients, and an absolute value of each of the plurality of deflection angles other than the first deflection angle is larger than the first deflection angle.

10. The ultrasound diagnostic apparatus according to claim 9, wherein the processing circuitry is further configured to acquire the received signals, each of the received signals corresponding to one of the plurality of reception scan lines, wherein the plurality of scan lines are generated by ultrasound scanning in which a plurality of reflected waves at the different deflection angles are received in response to the ultrasound transmission.

11. The ultrasound diagnostic apparatus according to claim 9, wherein the processing circuitry is further configured to calculate the coefficients based on mean values of the first signal values or the first pixel values.

12. The ultrasound diagnostic apparatus according to claim 11, wherein the processing circuitry is further configured to calculate the coefficients using an exponentiation function.

13. The ultrasound diagnostic apparatus according to claim 9, wherein the processing circuitry is further configured to calculate the coefficients based on local cross-correlation coefficient values calculated from the plurality of pieces of ultrasound image data, based on difference values of the plurality of pieces of ultrasound image data, or based on the difference values and mean values of the plurality of pieces of ultrasound image data.

14. The ultrasound diagnostic apparatus according to claim 13, wherein the processing circuitry is further configured to calculate the coefficients using an exponentiation function.

15. The ultrasound diagnostic apparatus according to claim 9, wherein the compounding comprises weighted addition.

16. An ultrasound diagnostic apparatus, comprising:
processing circuitry configured to
acquire, as a first data group, a plurality of pieces of ultrasound image data, each of the plurality of pieces of ultrasound image data being acquired at a different deflection angle, of a plurality of different deflection angles generated by first ultrasound scanning in a first mode in which the deflection angles for ultrasound transmission and reception are changed between a plurality of frames, the plurality of different deflection angles including a first deflection angle and each piece of ultrasound image data corresponding to a frame of the plurality of frames, acquire, as a second data group, first received signals, each of the first received signals corresponding to one of a plurality of reception scan lines, the first received signals being generated by second ultrasound scanning in a second mode in which the deflection angles for ultrasound transmission and reception are changed, and acquire, as a third data group, second received signals, each of the second received signals corresponding to one of the plurality of reception scan lines, the second received signals being generated by third ultrasound scanning in a third mode in which a plurality of reflected waves at the different deflection angles for ultrasound reception are received;
in the first mode, calculate first coefficients, each first coefficient corresponding to a spatial position of a plurality of spatial positions in a first piece of ultrasound image data and being separately calculated for each spatial position, of the acquired plurality of pieces of ultrasound image data, acquired at the first deflection angle, each of the first coefficients being calculated based on a signal value or a pixel value at a corresponding spatial position, of the plurality of spatial positions, in at least one of the acquired plurality of pieces of ultrasound image data acquired at a deflection angle, of the plurality of different deflection angles, other than the first deflection angle, and in the second and the third modes, calculate second coefficients, each second coefficient corresponding to one depth of a plurality of depths on a first reception scan line corresponding to the first deflection angle, each second coefficient being separately calculated for each one depth, the second coefficient being calculated based on a first signal value or a first pixel value at the one depth and being derived from the first received signals, when in the second mode, or the second received signals, when in the third mode, corresponding to at least one reception scan line, of the plurality of reception scan lines, having a deflection angle other than the first deflection angle;

in the first ultrasound scanning, multiply, by the first coefficients, second signal values or second pixel values corresponding to the plurality of spatial positions in the first piece of ultrasound image data corresponding to the first deflection angle, or third signal values or third pixel values corresponding to the plurality of spatial positions in a piece of image data that is obtained by compounding the plurality of pieces of ultrasound image data acquired at the plurality of different deflection angles including the first deflection angle, and in the second ultrasound scanning and the third ultrasound scanning, multiply, by the second coefficients, fourth signal values or fourth pixel values derived from the first received signals, when in the second mode, or the second received signals, when in the third mode, corresponding to the first reception scan line or a signal obtained by compounding the first received signals, when in the second mode, or the second received signals, when in the third mode, corresponding to the reception scan lines at the plurality of deflection angles including the first deflection angle, the fourth signal values or the fourth pixel values having values at the plurality of depths on the first reception scan line;

when the processing circuitry uses the first data group and at least one group of the second data group and the third group, (1) perform first multiplication, the first multiplication being multiplication of at least one of the data values in the first data group by at least one of the first coefficients, and/or (2) perform second multiplication, the second multiplication being multiplication of at least one of the data values in the at least one group by at least one of the second coefficients;

when the processing circuitry does not use the first data group and uses the second data group and the third data group are obtained, perform third multiplication, the third multiplication being multiplication of at least one of the data values in the at least one of the second data group and the third data group by at least one of the second coefficients;

when the processing circuitry uses the first data group, but does not perform the first multiplication, perform a compounding process on the first data group;

when the processing circuitry does not use the second data group, but does not perform the second multiplication nor the third multiplication, perform a compounding process on the second data group; and when the processing circuitry uses the third data group, but does not perform the second multiplication nor the third multiplication on the third data group, perform a compounding process on the third data group.

17. An ultrasound imaging method, comprising:

acquiring, by processing circuitry, a plurality of pieces of ultrasound image data, each of the plurality of pieces of ultrasound image data being acquired at a different deflection angle, of a plurality of different deflection angles, for both of ultrasound transmission and reception, the plurality of different deflection angles including a first deflection angle;

calculating, by the processing circuitry, coefficients, each coefficient corresponding to a spatial position of a plurality of spatial positions in a first piece of ultrasound image data, of the acquired plurality of pieces of ultrasound image data, acquired at the first deflection angle, each of the coefficients being calculated based on a signal value or a pixel value at a corresponding spatial position in at least one of the acquired plurality of pieces of ultrasound image data acquired at a deflection angle, of the plurality of different deflection angles, other than the first deflection angle, each coefficient being separately calculated for each spatial position;

generating an output image by multiplying, by the coefficients, signal values or pixel values corresponding to the plurality of spatial positions in the first piece of ultrasound image data acquired at the first deflection angle, or signal values or pixel values corresponding to the plurality of spatial positions in a piece of image data that is obtained by compounding the plurality of pieces of ultrasound image data acquired at the plurality of different deflection angles including the first deflection angle; and causing a display to display the output image, wherein the first piece of ultrasound image data acquired at the first deflection angle is not used for calculating the coefficients, and an absolute value of the each of deflection plurality of angles other than the first deflection angle is larger than the first deflection angle.

* * * * *